(12) United States Patent
Minden

(10) Patent No.: US 6,667,168 B1
(45) Date of Patent: *Dec. 23, 2003

(54) PAK4, A NOVEL GENE ENCODING A SERINE/THREONINE KINASE

(75) Inventor: Audrey Minden, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 97 days.

This patent is subject to a terminal disclaimer.

(21) Appl. No.: 09/718,032

(22) Filed: Nov. 21, 2000

Related U.S. Application Data

(63) Continuation of application No. PCT/US99/11341, filed on May 21, 1999, which is a continuation-in-part of application No. 09/082,737, filed on May 21, 1998, now Pat. No. 6,013,500.

(51) Int. Cl.$^7$ .......................... C12N 9/12; C12N 15/00; C12N 5/00; C12N 1/20; C07K 1/00

(52) U.S. Cl. ....................... 435/194; 435/6; 435/252.3; 435/320.1; 435/325; 530/350

(58) Field of Search .............................. 530/350, 320.1, 530/325, 252.3, 6; 435/194

(56) References Cited

U.S. PATENT DOCUMENTS

| | | | |
|---|---|---|---|
| 5,518,911 A | 5/1996 | Abo et al. | 435/194 |
| 5,605,825 A | 2/1997 | Abo et al. | 435/194 |
| 5,698,428 A | 12/1997 | Abo et al. | 435/194 |
| 5,698,445 A | 12/1997 | Abo et al. | 435/325 |
| 6,013,464 A | 1/2000 | Abo et al. | 435/15 |
| 6,013,500 A | 1/2000 | Minden | 435/194 |
| 6,048,706 A | 4/2000 | Abo et al. | 435/15 |
| 9,291,417 | 3/2003 | Plowman et al. | 514/12 |

OTHER PUBLICATIONS

Aspenstrom, P. et al. (1996) Two GTPases, Cdc42 and Rac, bind directly to a protein implicated in the immunodeficiency disorder Wiskott–Aldrich syndrome. Curr. Biol. 6, 70–75 (Exhibit 9).

Bagrodia, S. et al. (1995) Cdc42 and PAK–mediated signaling leads to Jun kinase and p38 mitogen–activated protein kinase activation, J. Biol. Chem. 270, 27995–27998 (Exhibit 10).

Bashour, A.M. et al. (1997) IQGAP1, a Rac–and Cdc42–binding protein, directly binds and cross–links microfilaments. J. Cell. Biol. 137, 1555–1566 (Exhibit 11).

Benner, G.E. et al. (1995) Activation of an S6/H4 kinase (PAK 65) from human placenta by intramolecular and intermolecular autophosphorylation, J. Biol. Chem. 270, 21121–21128 (Exhibit 12).

Bershadsky, A., and Futerman, A. (1994) Disruption of the Golgi apparatus by brefeldin a blocks cell polarization and inhibits directed cell migration. Proc. Natl. Acad. Sci. U.S.A. 91, 5686–5689 (Exhibit 13).

Brown, J. et al. (1996) Human Ste20 homologue hPak1 links GTPase to JNK MAP kinase pathway. Curr. Biol. 6, 598–605.

Burbelo, P.D. et al. (1995) A conserved binding motif defines numerous candidate target proteins for both Cdc42 and Rac GTPases. J. Biol. Chem. 270, 29071–29074 (Exhibit 14).

Coso, O.A. et al. (1995) The small GTP–binding proteins Racl and Cdc42 regulate the activity of the JNK/SAPK signaling pathway. Cell 81, 1137–1146 (Exhibit 15).

Cvrckova, F. et al. (1995) Ste20–like protein kinases are required for normal localization of cell growth and for cytokinesis in budding yeast. Genes Dev. 9, 1817–1830.

Dascher, C., and Balch, W.E. (1994) Dominant inhibitory mutants of ARF1 block endoplasmic reticulum to Golgi transport and trigger disassembly of the Golgi apparatus. J. Biol. Chem. 269, 1437–48 (Exhibit 16).

Dharmawardhane, S. et al. (1997) Localization of p21–activated kinase 1 (PAK1) to pinocytic vesicles and cortical actin structures in stimulated cells. J. Cell. Biol. 138, 1265–1278 (Exhibit 17).

(List continued on next page.)

*Primary Examiner*—Maryam Monshipouri
(74) *Attorney, Agent, or Firm*—John P. White; Cooper & Dunham LLP

(57) ABSTRACT

This invention provides an isolated mammalian nucleic acid molecule encoding a PAK4 serine/threonine kinase. This invention provides an isolated nucleic acid molecule encoding a mutant homolog of the mammalian PAK4 serine/threonine kinase whose amino acid sequence is set forth in FIG. 1A (SEQ ID NO: 2). This invention provides a fusion protein comprising a PAK4 serine/threonine kinase or a fragment thereof and a second peptide. This invention provides a purified mammalian PAK4 serine/threonine kinase. This invention provides a protein comprising substantially the amino acid sequence set forth in FIG. 1A. This invention provides a monoclonal antibody directed to an epitope of a PAK4 serine/threonine kinase. This invention provides a method of inhibiting PAK4 function comprising administering a ligand comprising an amino acid domain which binds to a GTP binding protein so as to inhibit binding of the GTP binding protein to PAK4. This invention provides a method of inhibiting PAK4 function comprising administering a ligand which binds to the GTP binding domain of PAK4 so as to inhibit PAK4 binding to a GTP binding protein. This invention provides a method of inhibiting PAK4 serine/threonine kinase function comprising administering a ligand which blocks an ATP binding domain so as to inhibit PAK4 serine/threonine kinase function. This invention provides a method of inhibiting growth of a tumor cell comprising blocking Cdc42Hs by administering a ligand capable of binding to a Cdc42Hs binding site of a PAK4 serine/threonine kinase.

2 Claims, 18 Drawing Sheets

OTHER PUBLICATIONS

Donaldson, J.G. et al. (1992) ADP–ribosylation factor, a small GTP–binding protein, is required for binding of the coatomer protein beta–COP to Golgi membranes. Proc. Natl. Acad. Sci. U.S.A. 89, 6408–6412 (Exhibit 18).

Donaldson, J.G. et al. (1992) Brefaldin A inhibits golgi membrane–catalysed exchange of guanine nucleotide into ARF protein. Nature 360, 350–352 (Exhibit 19).

Dutartre, H. et al. (1996) Cytokinesis arrest and redistribution of actin–cytoskeleton regulatory components in cells expressing the Rho GTPase CDC42HS. J. Cell. Sci. 109, 367–377 (Exhibit 20).

Erickson, J.W. et al. (1996) Mammalian Cdc42 is a brefeldin A–sensitive component of the Golgi apparatus. J. Biol. Chem. 271, 26850–26854.

Erickson, J.W. et al. (1997) Identification of an actin cytoskeletal complex that includes IQGAP and the Cdc42 GTPase. J. Biol. Chem. 272, 24443–24447 (Exhibit 21).

Fukata, M. et al. (1997) Regulation of cross–linking of actin filament by IQGAP1, a target for Cdc42. J. Biol. Chem. 272, 29579–29583 (Exhibit 22).

Hanks, S.K. et al. (1988) The protein kinase family: conserved features and deduced phylogeny of the catalytic domains. Science 241, 42–52 (Exhibit 23).

Harden, N. et al. (1996) A Drosophila homolog of the Rac–and Cdc42–activated serine/threone kinase PAK is a potential focal adhesion and focal complex protein that colocalizes with dynamic actin structures. Mol. Cell. Biol. 16, 1896–1908 (Exhibit 24).

Hart, M.J. et al. (1996) IQGAP,a calmodulin–binding protein with a rasGAP–related domain, is a potential effector for cdc4Hs. EMBO J. 15, 2997–3005 (Exhibit 25).

Helms, J.B., and Rothman, J.E. (1992) Inhibition by brefeldin A of a golgi membrane enzyme that catalyses exchange of guanine nucleotide bound t ARF. Nature 360, 352–354 (Exhibit 26).

Hillier, L. et al. (1995) yg22e03.rl Soars infant brain INIB Homo sapiens cDNA clone IMAGE:32974 5' similar to SP:KPAK–RAT p35465, EST Database Accession No. R18825 (Exhibit 27).

Johnson, L. et al. (1996) Active and inactive protein kinases: structural basis for regulation. Cell 85, 149–158 (Exhibit 28).

Joneson, T. et al. (1996) RAC regulation of actin polymerization and proliferation by a pathway distinct form Jun kinase. Science 274, 1374–1376 ( Exhibit 29).

Kozma, R. et al. (1995) The Ras–related protein Cdc42Hs and bradykinin promote formation of peripheral actin microspikes and filopodia in Swiss fibroblasts. Mol. Cell. Biol. 15, 1942–1952 (Exhibit 30).

Kuroda, S. et al. (1996) Identification of IQGAP as a putative target for the small GTPases, Cdc42 and Racl. J. Bio. Chem. 271, 23363–23367 (Exhibit 31).

Lamarche, N. et al. (1996) Rac and Cdc42 induce actin polymerization and G1 cell cycle prgression independently of p65PAK and the JNK/SAPK MAP 10 kinase cascade. Cell 87, 519–529 (Exhibit 32).

Manser, E. et al. (1993) A non–receptor tyrosine kinase that inhibits the GTPase activity of p21cdc42. Nature 363, 364–367 (Exhibit 33).

Manser, E. et al. (1994) A brain serine/threonine protein kinase activated by Cdc42 and Racl. Nature 367, 40–46.

Manser, E. et al. (1997) Expression of constitutively active alpha–PAK reveals effects of the kinase on actin and focal complexes. Mol. Cell. Biol. 17, 1129–1143 (Exhibit 34).

Manser, E. et al. (1998) PAK kinases are directly coupled to the PIX family of nucleotide exchange factors. Mol. Cell. 1, 183–192 (Exhibit 35).

Marshall, C.J. (1994) Signal transduction. Hot lips and phosphorylation of protein kinases. Nature 367, 686 (Exhibit 36).

Martin, G.A. et al. (1995) A novel serine kinase activated by racl/CDC42Hs–dependent autophosphorylation is related to PAK65 and STE20. EMBO J. 14, 1970–1978.

Melnik, M.M. (1997) GenBank Accession No. AF005046.

Minden, A. et al. (1994) Differential activation of ERK and JNK mitogen–activated protein kinases by Raf–1 and MEKK. Science 266, 1719–1723 (Exhibit 37).

Minden, A. et al. (1995) Selective activation of the JNK signaling cascade and c–Jun trancriptional activity by the small GTPases Rac and Cdc42Hs. Cell 81, 1147–1157 (Exhibit 38).

Nobes, C.D., and Hall, A. (1995) Rho. rac, and cdc42 GTPases regulate the assembly of multimolecular focal complexes associated with actin stress fibers, lamellipodia, and filopodia. Cell 81, 53–62 (Exhibit 39).

Orci, L. et al., (1991) Brefeldin A, a drug that blocks secretion, prevents the assembly of non–clathrin–coated buds on Golgi cisternae. Cell 64, 1183–1195 (Exhibit 40).

Pelech, S.L. (1996) Kinase connections on the cellular intranet. Signalling pathways. Curr. Biol. 6, 551–554 (Exhibit 41).

Teramoto, H. et al. (1996) Signaling form the small GTP–binding proteins Racl and Cdc42 to the c–Jun N–terminal kinase/stress–activated protein kinase pathway. A role for mixed lineage kinase 3/protein–tyrosine kinase 1, a novel member of the mixed lineage kinase family. J. Biol. Chem. 271, 27225–277228 (Exhibit 48).

Van Aelst, L. et al. (1996) Identifcation of a novel Rac1–interacting protein involved in membrane ruffling. EMBO J. 15, 3778–3786 (Exhibit 49).

Van Aelst, L., and D'Souza–Schorey, C. (1997) Rho GTPases and signaling networks. Genes Dev. 11, 2295–2322 (Exhibit 50).

Westwick, J.K. et al. (1997) Rac regulation of tranformation, gene expression, and actin organization by multiple, PAK–Independent pathways. Mol. Cell. Biol 17, 1324–1335 (Exhibit 51).

Zhang, C. J. et al. (1994) Expression of a dominant allele of human ARF1 inhibits membrane traffic in vivo. J. Cell. Biol. 124, 289–300 (Exhibit 52).

Zhang, F. et al. (1994) Atomic structure of the MAP kinase ERK2 at 2.3 A resolution. Nature 367, 704–711 (Exhibit 53).

Zhang, S. et al. (1995) Rho family GTPases regulate p38 mitogen–activated protein kinase through the downstream mediator Pak1. J. Biol. Chem. 270, 23934–23936 (Exhibit 54).

FIGURE 1A

```
         GGCGCGGAGTTCCAGTTCGAGCAGTTAGGCCGCGAGCGACTGCGGCGCCGATGAGTAACCGAAGCCCT
         AGAGAGTGGTCACCTGCCTCTGAGGGCACTTCTGTCCACATCAGACCCAGCCGCACCGAGTCCCGGCACC
   1     ATGTTTGGGAAGAGGAAGAAGCGGGTGGAGATCTCCGCGCCGTCCAACTTCGAGCACCGCGTGCACGGCTTC
         M  F  G  K  R  K  K  R  V  E  I  S  A  P  S  N  F  E  H  R  V  H  G  F
  76     GACCAGCACGAGCAGAAGTTCACGGGGCTGCCCCGGCAGTGGCAGAGCCTGATCGAGGAGTCGGCTCGCCGGCCC
         D  Q  H  E  Q  K  F  T  G  L  P  R  Q  W  Q  S  L  I  E  E  S  A  R  R  P
 151     AAGCCCCTCGTCGACCCCGCCTGCATCACCTCCATCCAGCCCGGGCCCCAAGACCATCGTGCGGGGCAGCAAA
         K  P  L  V  D  P  A  C  I  T  S  I  Q  P  G  A  P  K  T  I  V  R  G  S  K
 226     GGTGCCAAAGATGGGGCCCTCACGCTGCTGCTGGACGAGTTTGAGAACATGTCGGTGACACGCTCCAACTCCCTG
         G  A  K  D  G  A  L  T  L  L  L  D  E  F  E  N  M  S  V  T  R  S  N  S  L
 301     CGGAGAGACAGCCCCGGCCCGCCCCGTGCCCGCAGAAAATGGGATGCCAGAGGAGCCAGCCACCACGGCC
         R  R  D  S  P  P  P  P  A  R  A  R  Q  E  N  G  M  P  E  E  P  A  T  T  A
 376     AGAGGGGCCCAGGGAAGGCAGCCGGGCCCGTTCGCCGGTCACAGCGAGGCAGGTGGCGGCAGTGGGTGAC
         R  G  G  P  G  K  A  G  S  R  G  R  F  A  G  H  S  E  A  G  G  G  S  G  D
 451     AGGCGACGGGCGGGGCCCAGAGAAGAGGCCCAAGTCTTCCGGAGGGCTCTTCAGGGGTCTCCCCAGGAGTCCTCCCGG
         R  R  R  A  G  P  E  K  R  P  K  S  S  R  E  G  S  G  P  Q  E  S  S  R
 526     GACAAACGCCCCCTCTCCGGGCCTGATGTCGGGACCCCGCAGCCTGCCAGTGGGGCGAAACTGGCA
         D  K  R  P  L  S  G  P  D  V  G  T  P  Q  P  A  G  L  A  S  G  A  K  L  A
 601     GCTGGCCGGCCCTTTAACACCTACCCGAGGGCTGACACGGACCACCCATCCCGGGGTGCCCAGGGGAGCCTCAT
         A  G  R  P  F  N  T  Y  P  R  A  D  T  D  H  P  S  R  G  A  Q  G  E  P  H
 676     GACGTGGCCCCCTAACGGGCCCATCAGGGCCTTGGCCATCCCCCAGTCCTCCTCCCGGCCTCCC
         D  V  A  P  N  G  P  S  A  G  G  L  A  I  P  Q  S  S  S  S  R  P  P
 751     ACCCGAGCCCGAGGTGCCCCCAGCTGCTGGGAGTGCTGGGGCCTGTGCTGGGCCCTCACGAGCCCCAGCC
         T  R  A  R  G  A  P  S  P  G  V  L  G  P  H  A  S  E  P  Q  L  A  P  P  A
 826     TGCACCCCCGCCGCCGCCCCTGCTGTTCCGGGCCCTGCCCTGCAGCTGCCTCCACCAGCGGAGTATCC
         C  T  P  A  A  A  P  A  V  P  G  P  P  P  P  G  P  R  S  P  Q  R  V  S
 901     CATGAGCAGTTCCGGGCGGCTCCGCAGCTGGTGTGCAGCTGCCATGGACCCCTACCTGGACAACTTCATC
         H  E  Q  F  R  A  A  L  Q  L  V  V  D  P  P  G  D  D  P  R  S  Y  L  D  N  E  I
 976     AAGATTGGCGAGGGCTCCACGGCTCCATCGTGTGCATCGCCACCGTGCGCAGTGGCAAGCTGGTGGCCGTCAAG
         K  I  G  E  G  S  T  G  I  V  C  I  A  T  V  R  S  G  K  L  V  A  V  K
1051     AAGATGGACCTGCGCAAGCAGCAGAGGCGCGAGCTGCTCTTCAACGAGGTGGTAATCATGAGGGACTACCAGCAC
         K  M  D  L  R  K  Q  Q  R  R  E  L  L  F  N  E  V  V  I  M  R  D  Y  Q  H
1126     GAGAATGTGGTGGTGGAGATGTACAACAGTAGCTACCTGGTGGGGGGACGAGCTCTGGTCATGAGTTCCTGAAGGA
```

FIGURE 1B

```
                 E  N  V  V  E  M  Y  N  S  Y  L  V  G  D  E  L  W  V  V  M  E  F  L  E  G                    400
1201   GGCGCCCTCACCGACATGTCACCCACACCAGGATGAACGAGGAGCAGATCGCGGCCGTGTGCCTTGCAGTGCTG
        G  A  L  T  D  V  T  H  T  R  M  N  E  E  Q  I  A  A  V  C  L  A  V  L                               425
1276   CAGGCCCTGTCGGTGCTCCACGCCCAGGGCGTCATCCAGGGACTCGATCCTGCTGACCCAT
        Q  A  L  S  V  L  H  A  Q  G  V  I  H  R  D  I  K  S  D  I  L  L  T  H                                450
1351   GATGGCAGGGTGAAGCTGTCAGACTTTGGTTTCTGCGCCCAGGTGAGCAAGGAAGTGCCCCGAAGGAAGTCGCTG
        D  G  R  V  K  L  S  D  F  G  F  C  A  Q  V  S  K  E  V  P  R  R  K  S  L                             475
1426   GTCGGCACGCCCTACTGGATGGCCCCAGAGCTCATCTCCCGCCTTCCCTACGGGCCAGAGGTAGACATCTGGTCG
        V  G  T  P  Y  W  M  A  P  E  L  I  S  R  L  P  Y  G  P  E  V  D  I  W  S                             500
1501   CTGGGGATAATGGTGATTGAGATGGTGGACGGAGAGCCCCCTACTTCAACGAGCCACCCTCAAAGCCATGAAG
        L  G  I  M  V  I  E  M  V  D  G  E  P  P  Y  F  N  E  P  P  L  K  A  M  K                             525
1576   ATGATTCGGGACAACCTGCCACCCGACTGAAGAACCTGCACAAGGTGTCGCCATCCCTGAAGGGCTTCCTGGAC
        M  I  R  D  N  L  P  P  R  L  K  N  L  H  K  V  S  P  S  L  K  G  F  L  D                             550
1651   CGCCTGCTGGTCCGAGACCCTGCTGCCGAGCGGGCCACGGCCGAGCTGCTGAAGCACCCATTCCTGGCCAAGGCA
        R  L  L  V  R  D  P  A  Q  R  A  T  A  A  E  L  L  K  H  P  F  L  K  A                                575
1726   GGGCCGCCTGCCAGCATCGTGCCCCTCATGCGCCAGAACCGCACGACGATGA
        G  P  P  A  S  I  V  P  L  M  R  Q  N  R  T  R  *                                                     591
```

FIGURE 1C

```
                                                                                    III
PAK4   324  PIKIGEGSTGIVCIATVRSSGKLVAVKKMDLRKQQRRELLFNEVVIMRDY  373
PAK2   251  YEKIGQGASGTVFTATDVALGQEVAIKQINLQKQPKKELINEILLVMKEL   300
STE20  623  LVKIGQGASGGVYTAYEIGTNVSVAIKQMNLEKQPKKELLINEILVMRGS   672

IV                                                                    VIa
PAK4   374  QHENVVEMYNSYLVGDELWVVMEFLEGGALTDIVTHTRMNEEQIAAVCLA   423
PAK2   301  KNPNIVNFLDSYLVGDELWVVMEYLAGRSLTDVVTETCMDEAQIAAVCRE   350
STE20  674  KHPNIVNFIDSYVLKGDLWVIMEYMEGGSLTDVVTHCILTEGQIGAVCRE   723

VIb                                VII
PAK4   424  VLQALSVLHAQGVIHRDIKSDSILLTHDGRVKLSDFGFCAQVSKEVPRRK   473
PAK2   351  CLQALEFLHANQVIHRDIKSDNVLLGMEGSVKLTDFGFCAQITPEQSKRS   400
STE20  724  TLSGLEFLHSKGVLHRDIKSDNILLSMEGDIKLTDFGFCAQINELNLKRT   773

VIII                                         IX
PAK4   474  SLVGTPYWMAPELISRLPYGPEVDIWSLGIMVIEMVDGEPPYFNEPPLKA   523
PAK2   401  TMVGTPYWMAPEVVTRKAYGPKVDIWSLGIMAIEMVEGEPPYLNENPLRA   450
STE20  774                                                         823

X                                                                    XI
PAK4   524  MKMIRKNLPPRLKNLHKVSPSLKGFLDRLLVRDPAQRATAAELLKHPFLA   573
PAK2   451  LYLIATNGTPELQNPEKLSPIFRDFLNRCLEMDVEKRGSAKELLQHPFLK   500
STE20  824                                                         873
```

FIGURE 1D

| | | |
|---|---|---|
| PAK4 | 10 EISAPSNFEHRVHTGFDQHEQ 30 |
| PAK2 | 71 EISPPSDFEHTIHVGFDAVTG 91 |
| STE20 | 317 ISYNA--KIHHVGVDSKTG 362 |
| WASP | 238 DIGAPSGFKHVSHVGWDPQNG 258 |
| CLA4 | 183 GVSSPTNFTHKVHVGFDPETG 203 |

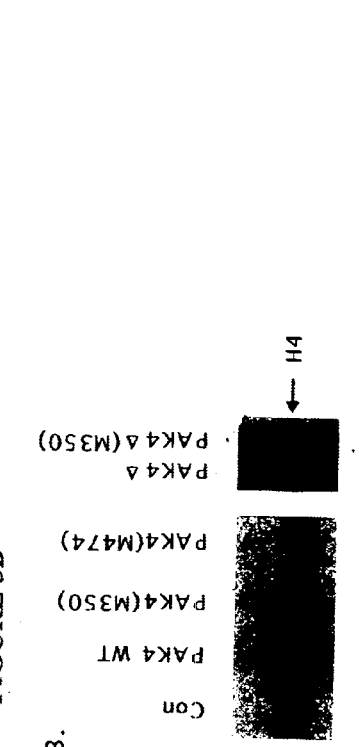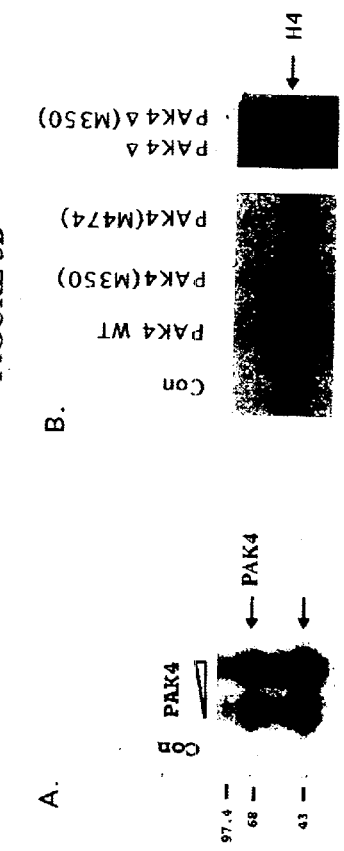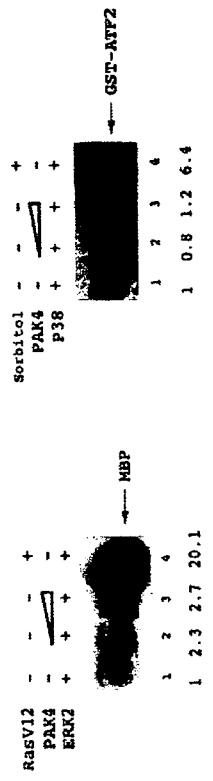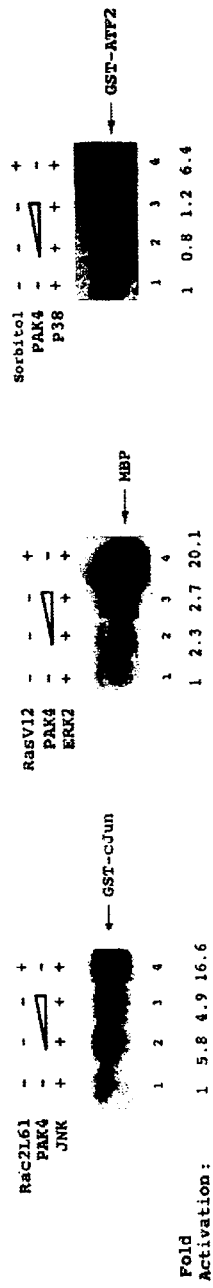
FIGURE 3A
FIGURE 3B
FIGURE 3C
FIGURE 3D
FIGURE 3E Anti-HA
PAK4

Actin

PAK4/
CDC42HsV12

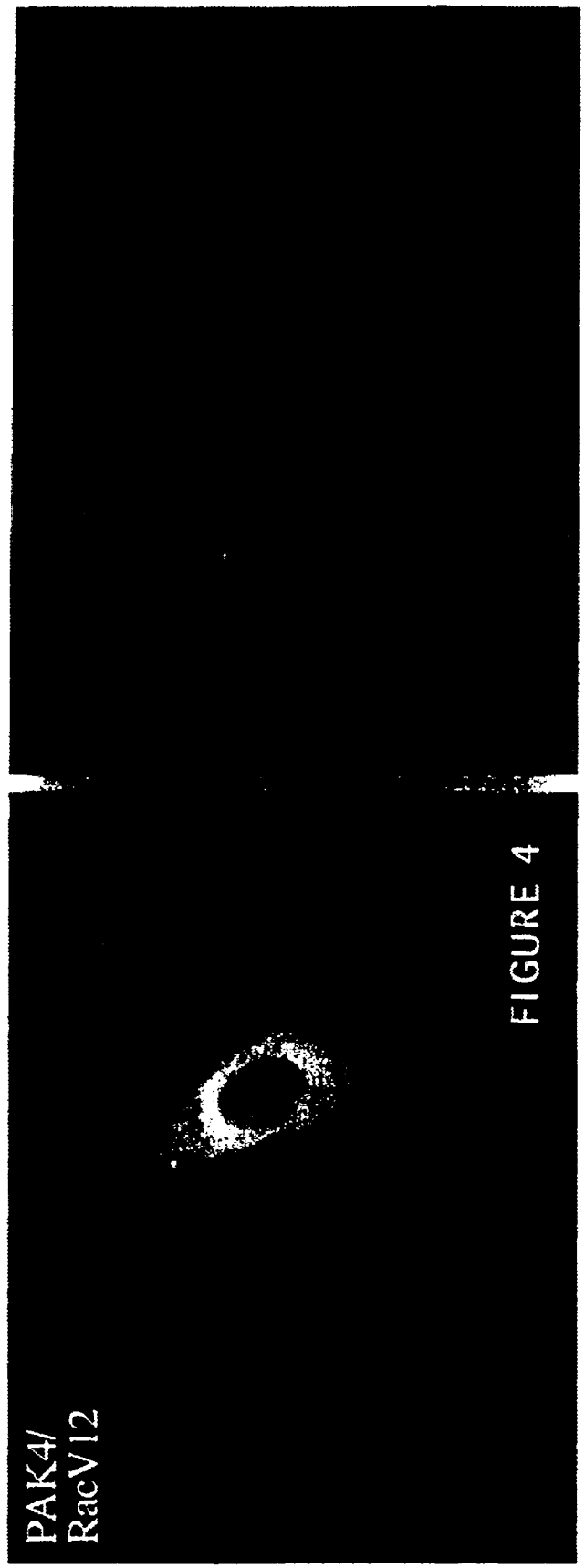

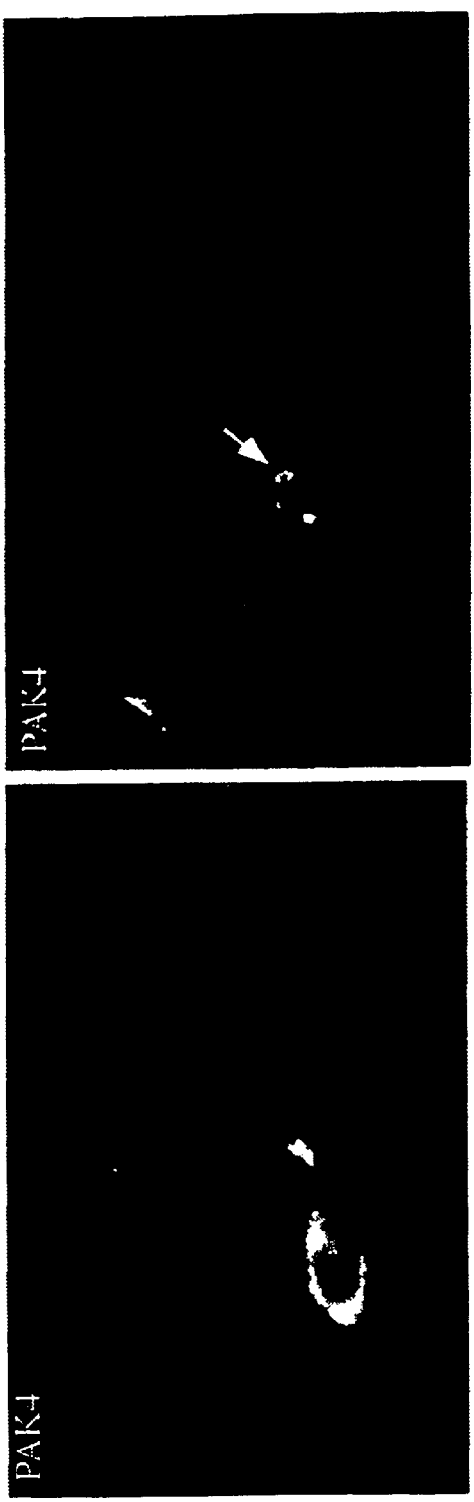
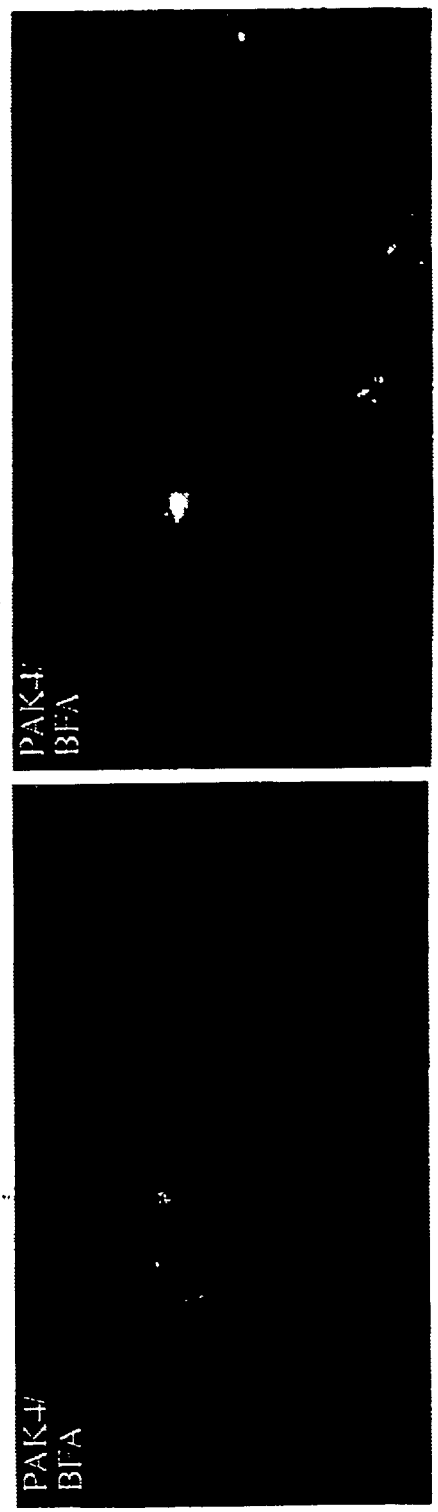
FIGURE 5A  Anti-HA
FIGURE 5B  Anti-β-COP
FIGURE 5C
FIGURE 5D

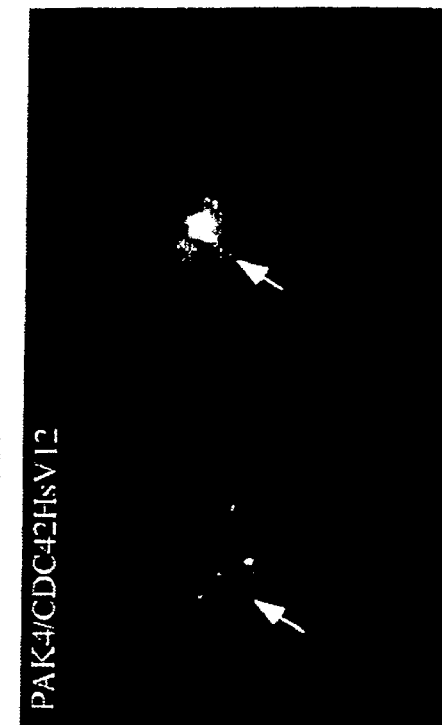
FIGURE 5E
*Anti-β-COP*
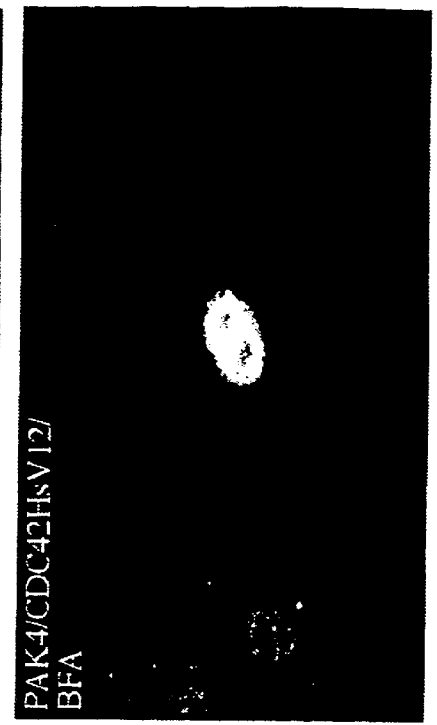
FIGURE 5F
*Anti-HA*
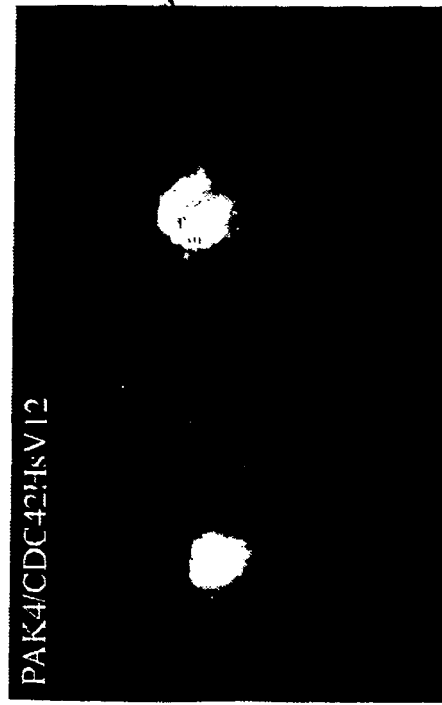
FIGURE 5G
FIGURE 5H

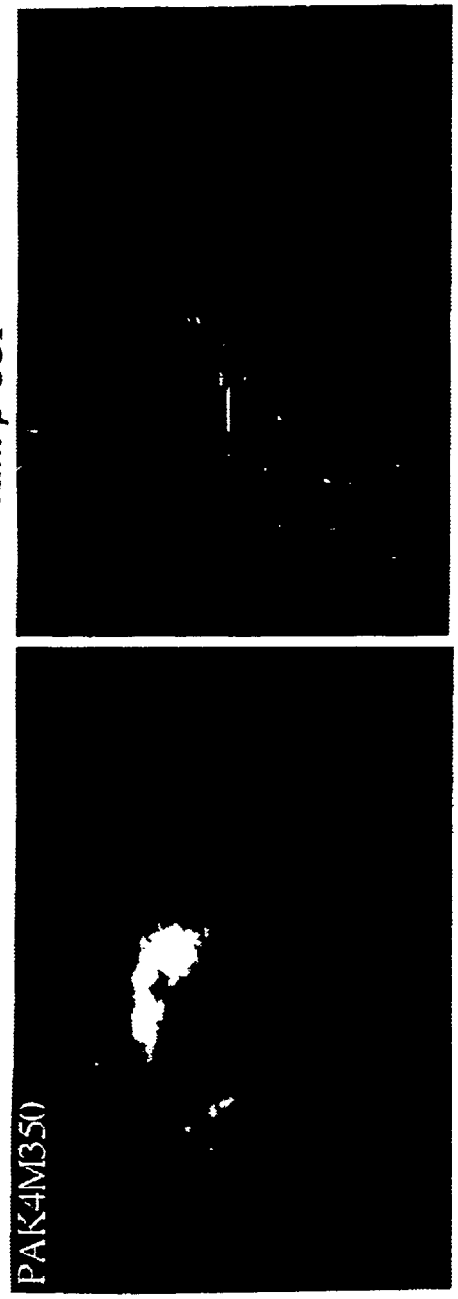
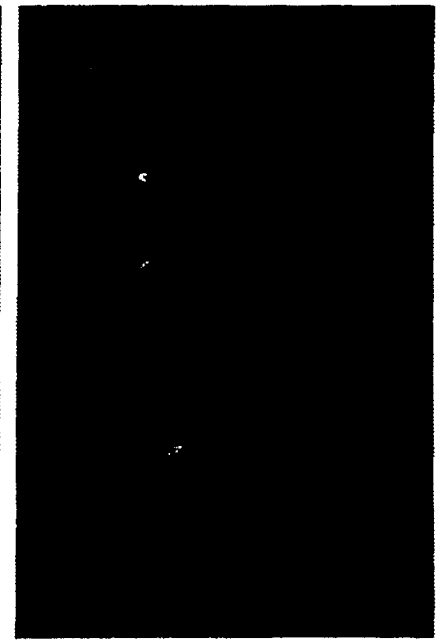
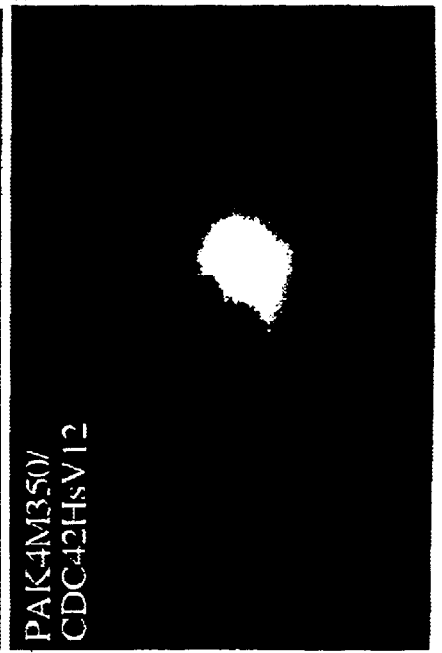
FIGURE 6A Anti-HA
FIGURE 6B Anti-β-COP
FIGURE 6C
FIGURE 6D

*FIGURE 6E*
*Anti-HA*
*FIGURE 6F*
*Actin*
PAK4E474
PAK4E474/
CDC42HsV12
*FIGURE 6G*
*FIGURE 6H*

*Anti-HA*

PAK4 + Cdc42L61C40

FIGURE 8A    Partial cDNA of the mouse PAK4:

AAGCAGCAGC GGCGCGAGTT GCTCTTCAAT GAGGTGGTGA TCATGCGGGA
CTACGGGCAC GAGAACGTGG TGGAGATGTA CAACAGTAC CTGGTGGGTG
ACGAACTCTG GGTCGTCATG GAGTTCCTGG AAGGCGGCGC CCTCACGGAT
ATTGTCACCC ACACCAGGAT GAACGAGGAA CAGATCGCCG CCGTGTGCCT
GGCTGTGCTT CAGGGGCTGG CTGTGCTCCA CGCCCAGGGT GTCATCCACA
GCGACATAAA AACGGACA predicted amino acid sequence of the partial mouse PAK4 cDNA:

FIGURE 8B    KQQRRELLFN EVVIMRDYRH ENVVEMYNSY LVGDELWVVM EFLEGGALTD
IVTHTRMNEE QIAAVCLAVL QALAVLHAQG VIHSDIKTD

Partial genomic sequence of mouse PAK4:

FIGURE 8C    ACCTGGTGGG TGACGAACTC TGGGTCGTCA TGGAGTTCCT GGAAGGCGGC
GCCCTCACGG ATATTGTCAC CCACACCAGG TACCATAGGG CAGCCTGCTG
GCTCATGTGC TCCCTGGGGT GGAACTGGGA CCCTTTAGGC TCTGGTGATA
GACAAGTGCC CTCCAGAGTG TGGGTGGGGC AGTGAGGCCA GGCACACAGG
ATGGGGGTCA TAGCATCGTG GCTCCCTGAC CCCTGTTGAG GCGGGTCTTT
GTGACCTCTT GTTGTCT AAA GCAGGGT AGG GGCCTCTTCA CTGCCCACTC
TCACCCCAGG GTGGGATGCC CAAGGCAGCG CTGAGTGCCC AGTTGCTCCT
CTGCCCGGCC AGGATGAACG AGGAAACAGA T CGCCGCCGT GTGCCTGGCT
TGTGCTTCAN GGGCTGGCTT GTGCTCCACG CCCAGGGTGT CATCCACCGT
GACATCAAGA GTGACTCTAT CTTGCTGACC CATGATGGC

SEQUENCE LISTING

<160> NUMBER OF SEQ ID NOS: 17

<210> SEQ ID NO 1
<211> LENGTH: 1940
<212> TYPE: DNA
<213> ORGANISM: human

<400> SEQUENCE: 1

```
tgagggaggc gcgagggcgc ggagttccag gtcgagcagt taggccgcga gcgactgcgg      60
cgccgagccg atgagtaacc cgaagcccct agaggagtgg tcacctgcct gagggcactt     120
ctgtcccacc agcatcagac caggccgcac cgagtccccg gcaccatgtt tgggaagagg     180
aagaagcggg tggagatctc cgcgccgtcc aacttcgagc accgcgtgca cacgggcttc     240
gaccagcacg agcagaagtt cacggggctg ccccgccagt ggcagagcct gatcgaggag     300
tcggctcgcc ggcccaagcc cctcgtcgac cccgcctgca tcacctccat ccagcccggg     360
gcccccaaga ccatcgtgcg gggcagcaaa ggtgccaaag atgggccct cacgctgctg     420 ctggacgagt ttgagaacat gtcggtgaca cgctccaact ccctgcggag agacagcccg     480
ccgccgcccg cccgtgcccg ccaggaaaat gggatgccag aggagccggc caccacggcc     540 agaggggcc cagggaaggc aggcagccga ggccggttcg ccggtcacag cgaggcaggt     600
ggcggcagtg tgacaggcg acgggcgggg ccagagaaga ggcccaagtc ttccagggag     660
ggctcagggg gtccccagga gtcctcccgg gacaaacgcc ccctctccgg gcctgatgtc     720 ggcaccccc agcctgctgg tctggccagt ggggcgaaac tggcagctgg ccggcccttt     780
aacacctacc cgagggctga cacggaccac ccatcccggg gtgcccaggg ggagcctcat     840
gacgtggccc ctaacgggcc atcagcgggg ggcctggcca tccccagtc ctcctcctcc     900 tcctcccggc ctcccacccg agcccgaggt gcccccagcc ctggagtgct gggaccccac     960
gcctcagagc cccagctggc ccctccagcc tgcacccccg ccgccctgc tgttcctggg    1020 cccctggcc cccgctcacc acagcgggag ccacagcgag tatcccatga gcagttccgg    1080
gctgccctgc agctggtggt ggacccaggc gaccccgct cctacctgga caacttcatc    1140
agattggcga gggctccacg ggcatcgtgt gcatcgccac cgtgcgcagc tcgggcaagc    1200
tggtggccgt caagaagatg gacctgcgca agcagcagag gcgcgagctg ctcttcaacg    1260
aggtggtaat catgagggac taccagcacg agaatgtggt ggagatgtac aacagctacc    1320
tggtggggga cgagctctgg gtggtcatgg agttcctgga aggaggcgcc ctcaccgaca    1380 tcgtcacccca caccaggatg aacgaggagc agatcgcggc cgtgtgcctt gcagtgctgc    1440
aggccctgtc ggtgctccac gcccaggcg tcatccaccg ggacatcaag agcgactga    1500 tcctgctgac ccatgatggc agggtgaagc tgtcagactt tgggttctgc gcccaggtga    1560
```

-continued

```
gcaaggaagt gccccgaagg aagtcgctgg tcggcacgcc ctactggatg cccccagagc    1620
tcatctcccg ccttccctac gggccagagg tagacatctg gtcgctgggg ataatggtga    1680
ttgagatggt ggacggagag cccccctact tcaacgagcc accccctcaaa gccatgaaga   1740 tgattcggga caacctgcca ccccgactga agaacctgca caaggtgtcg ccatccctga    1800
agggcttcct ggaccgcctg ctggtgcgag accctgccca gcgggccacg gcagccgagc    1860
tgctgaagca cccattcctg gccaaggcag ggccgcctgc cagcatcgtg cccctcatgc    1920
gccagaaccg caccagatga                                                1940
```

<210> SEQ ID NO 2
<211> LENGTH: 591
<212> TYPE: PRT
<213> ORGANISM: human

<400> SEQUENCE: 2

```
Met Phe Gly Lys Arg Lys Lys Arg Val Glu Ile Ser Ala Pro Ser Asn
 1               5                  10                  15

Phe Glu His Arg Val His Thr Gly Phe Asp Gln His Glu Gln Lys Phe
            20                  25                  30

Thr Gly Leu Pro Arg Gln Trp Gln Ser Leu Ile Glu Glu Ser Ala Arg
        35                  40                  45

Arg Pro Lys Pro Leu Val Asp Pro Ala Cys Ile Thr Ser Ile Gln Pro
    50                  55                  60

Gly Ala Pro Lys Thr Ile Val Arg Gly Ser Lys Gly Ala Lys Asp Gly
65                  70                  75                  80

Ala Leu Thr Leu Leu Leu Asp Glu Phe Glu Asn Met Ser Val Thr Arg
                85                  90                  95

Ser Asn Ser Leu Arg Arg Asp Ser Pro Pro Pro Ala Arg Ala Arg
            100                 105                 110

Gln Glu Asn Gly Met Pro Glu Pro Ala Thr Thr Ala Arg Gly Gly
            115                 120                 125

Pro Gly Lys Ala Gly Ser Arg Gly Arg Phe Ala Gly His Ser Glu Ala
    130                 135                 140

Gly Gly Gly Ser Gly Asp Arg Arg Ala Gly Pro Glu Lys Arg Pro
145                 150                 155                 160

Lys Ser Ser Arg Glu Gly Ser Gly Gly Pro Gln Glu Ser Ser Arg Asp
                165                 170                 175

Lys Arg Pro Leu Ser Gly Pro Asp Val Gly Thr Pro Gln Pro Ala Gly
            180                 185                 190

Leu Ala Ser Gly Ala Lys Leu Ala Ala Gly Arg Pro Phe Asn Thr Tyr
        195                 200                 205

Pro Arg Ala Asp Thr Asp His Pro Ser Arg Gly Ala Gln Gly Glu Pro
    210                 215                 220

His Asp Val Ala Pro Asn Gly Pro Ser Ala Gly Leu Ala Ile Pro
225                 230                 235                 240

Gln Ser Ser Ser Ser Ser Arg Pro Pro Thr Arg Ala Arg Gly Ala
                245                 250                 255

Pro Ser Pro Gly Val Leu Gly Pro His Ala Ser Glu Pro Gln Leu Ala
            260                 265                 270

Pro Pro Ala Cys Thr Pro Ala Ala Pro Ala Val Pro Gly Pro Pro Gly
        275                 280                 285

Pro Arg Ser Pro Gln Arg Glu Pro Gln Arg Val Ser His Glu Gln Phe
    290                 295                 300
```

-continued

```
Arg Ala Ala Leu Gln Leu Val Val Asp Pro Gly Asp Pro Arg Ser Tyr
305                 310                 315                 320

Leu Asp Asn Phe Ile Lys Ile Gly Glu Gly Ser Thr Gly Ile Val Cys
                325                 330                 335

Ile Ala Thr Val Arg Ser Ser Gly Lys Leu Val Ala Val Lys Lys Met
            340                 345                 350

Asp Leu Arg Lys Gln Gln Arg Arg Glu Leu Leu Phe Asn Glu Val Val
        355                 360                 365

Ile Met Arg Asp Tyr Gln His Glu Asn Val Val Glu Met Tyr Asn Ser
    370                 375                 380

Tyr Leu Val Gly Asp Glu Leu Trp Val Val Met Glu Phe Leu Glu Gly
385                 390                 395                 400

Gly Ala Leu Thr Asp Ile Val Thr His Thr Arg Met Asn Glu Glu Gln
                405                 410                 415

Ile Ala Ala Val Cys Leu Ala Val Leu Gln Ala Leu Ser Val Leu His
            420                 425                 430

Ala Gln Gly Val Ile His Arg Asp Ile Lys Ser Asp Ser Ile Leu Leu
        435                 440                 445

Thr His Asp Gly Arg Val Lys Leu Ser Asp Phe Gly Phe Cys Ala Gln
    450                 455                 460

Val Ser Lys Glu Val Pro Arg Arg Lys Ser Leu Val Gly Thr Pro Tyr
465                 470                 475                 480

Trp Met Ala Pro Glu Leu Ile Ser Arg Leu Pro Tyr Gly Pro Glu Val
                485                 490                 495

Asp Ile Trp Ser Leu Gly Ile Met Val Ile Glu Met Val Asp Gly Glu
            500                 505                 510

Pro Pro Tyr Phe Asn Glu Pro Pro Leu Lys Ala Met Lys Met Ile Arg
        515                 520                 525

Asp Asn Leu Pro Pro Arg Leu Lys Asn Leu His Lys Val Ser Pro Ser
    530                 535                 540

Leu Lys Gly Phe Leu Asp Arg Leu Leu Val Arg Asp Pro Ala Gln Arg
545                 550                 555                 560

Ala Thr Ala Ala Glu Leu Leu Lys His Pro Phe Leu Ala Lys Ala Gly
                565                 570                 575

Pro Pro Ala Ser Ile Val Pro Leu Met Arg Gln Asn Arg Thr Arg
            580                 585                 590

<210> SEQ ID NO 3
<211> LENGTH: 250
<212> TYPE: PRT
<213> ORGANISM: human

<400> SEQUENCE: 3

Phe Ile Lys Ile Gly Glu Gly Ser Thr Gly Ile Val Cys Ile Ala Thr
1               5                   10                  15

Val Arg Ser Ser Gly Lys Leu Val Ala Val Lys Lys Met Asp Leu Arg
                20                  25                  30

Lys Gln Gln Arg Arg Glu Leu Leu Phe Asn Glu Val Val Ile Met Arg
            35                  40                  45

Asp Tyr Gln His Glu Asn Val Val Glu Met Tyr Asn Ser Tyr Leu Val
        50                  55                  60

Gly Asp Glu Leu Trp Val Val Met Glu Phe Leu Glu Gly Gly Ala Leu
65                  70                  75                  80

Thr Asp Ile Val Thr His Thr Arg Met Asn Glu Glu Gln Ile Ala Ala
                85                  90                  95
```

-continued

Val Cys Leu Ala Val Leu Gln Ala Leu Ser Val Leu His Ala Gln Gly
            100                 105                 110

Val Ile His Arg Asp Ile Lys Ser Asp Ser Ile Leu Leu Thr His Asp
        115                 120                 125

Gly Arg Val Lys Leu Ser Asp Phe Gly Phe Cys Ala Gln Val Ser Lys
    130                 135                 140

Glu Val Pro Arg Arg Lys Ser Leu Val Gly Thr Pro Tyr Trp Met Ala
145                 150                 155                 160

Pro Glu Leu Ile Ser Arg Leu Pro Tyr Gly Pro Glu Val Asp Ile Trp
                165                 170                 175

Ser Leu Gly Ile Met Val Ile Glu Met Val Asp Gly Glu Pro Pro Tyr
            180                 185                 190

Phe Asn Glu Pro Pro Leu Lys Ala Met Lys Met Ile Arg Lys Asn Leu
        195                 200                 205

Pro Pro Arg Leu Lys Asn Leu His Lys Val Ser Pro Ser Leu Lys Gly
    210                 215                 220

Phe Leu Asp Arg Leu Leu Val Arg Asp Pro Ala Gln Arg Ala Thr Ala
225                 230                 235                 240

Ala Glu Leu Leu Lys His Pro Phe Leu Ala
                245                 250

<210> SEQ ID NO 4
<211> LENGTH: 250
<212> TYPE: PRT
<213> ORGANISM: human

<400> SEQUENCE: 4

Tyr Glu Lys Ile Gly Gln Gly Ala Ser Gly Thr Val Phe Thr Ala Thr
1               5                   10                  15

Asp Val Ala Leu Gly Gln Glu Val Ala Ile Lys Gln Ile Asn Leu Gln
            20                  25                  30

Lys Gln Pro Lys Lys Glu Leu Ile Ile Asn Glu Ile Leu Val Met Lys
        35                  40                  45

Glu Leu Lys Asn Pro Asn Ile Val Asn Phe Leu Asp Ser Tyr Leu Val
    50                  55                  60

Gly Asp Glu Leu Phe Val Val Met Glu Tyr Leu Ala Gly Arg Ser Leu
65                  70                  75                  80

Thr Asp Val Val Thr Glu Thr Cys Met Asp Glu Ala Gln Ile Ala Ala
            85                  90                  95

Val Cys Arg Glu Cys Leu Gln Ala Leu Glu Phe Leu His Ala Asn Gln
            100                 105                 110

Val Ile His Arg Asp Ile Lys Ser Asp Asn Val Leu Leu Gly Met Glu
        115                 120                 125

Gly Ser Val Lys Leu Thr Asp Phe Gly Phe Cys Ala Gln Ile Thr Pro
    130                 135                 140

Glu Gln Ser Lys Arg Ser Thr Met Val Gly Thr Pro Tyr Trp Met Ala
145                 150                 155                 160

Pro Glu Val Val Thr Arg Lys Ala Tyr Gly Pro Lys Val Asp Ile Trp
                165                 170                 175

Ser Leu Gly Ile Met Ala Ile Glu Met Val Glu Gly Glu Pro Pro Tyr
            180                 185                 190

Leu Asn Glu Asn Pro Leu Arg Ala Leu Tyr Leu Ile Ala Thr Asn Gly
        195                 200                 205

Thr Pro Glu Leu Gln Asn Pro Glu Lys Leu Ser Pro Ile Phe Arg Asp

```
            210                 215                 220
Phe Leu Asn Arg Cys Leu Glu Met Asp Val Glu Lys Arg Gly Ser Ala
225                 230                 235                 240

Lys Glu Leu Leu Gln His Pro Phe Leu Lys
                245                 250

<210> SEQ ID NO 5
<211> LENGTH: 250
<212> TYPE: PRT
<213> ORGANISM: yeast

<400> SEQUENCE: 5

Leu Val Lys Ile Gly Gln Gly Ala Ser Gly Gly Val Tyr Thr Ala Tyr
1               5                   10                  15

Glu Ile Gly Thr Asn Val Ser Val Ala Ile Lys Gln Met Asn Leu Glu
                20                  25                  30

Lys Gln Pro Lys Lys Glu Leu Ile Ile Asn Glu Ile Leu Val Met Lys
            35                  40                  45

Gly Ser Lys His Pro Asn Ile Val Asn Phe Ile Asp Ser Tyr Val Leu
        50                  55                  60

Lys Gly Asp Leu Trp Val Ile Met Glu Tyr Met Glu Gly Gly Ser Leu
65                  70                  75                  80

Thr Asp Val Val Thr His Cys Ile Leu Thr Glu Gly Gln Ile Gly Ala
                85                  90                  95

Val Cys Arg Glu Thr Leu Ser Gly Leu Glu Phe Leu His Ser Lys Gly
            100                 105                 110

Val Leu His Arg Asp Ile Lys Ser Asp Asn Ile Leu Leu Ser Met Glu
        115                 120                 125

Gly Asp Ile Lys Leu Thr Asp Phe Gly Phe Cys Ala Gln Ile Asn Glu
130                 135                 140

Leu Asn Leu Lys Arg Thr Thr Met Val Gly Thr Pro Tyr Trp Met Ala
145                 150                 155                 160

Pro Glu Val Val Ser Arg Lys Glu Tyr Gly Pro Lys Val Asp Ile Trp
                165                 170                 175

Ser Leu Gly Ile Met Ile Ile Glu Met Ile Glu Gly Glu Pro Pro Tyr
            180                 185                 190

Leu Asn Glu Thr Pro Leu Arg Ala Leu Tyr Leu Ile Ala Thr Asn Gly
        195                 200                 205

Thr Pro Lys Leu Lys Glu Pro Glu Asn Leu Ser Ser Leu Lys Lys
            210                 215                 220

Phe Leu Asp Trp Cys Leu Cys Val Glu Pro Glu Asp Arg Ala Ser Ala
225                 230                 235                 240

Thr Glu Leu Leu His Asp Glu Tyr Ile Thr
                245                 250

<210> SEQ ID NO 6
<211> LENGTH: 21
<212> TYPE: PRT
<213> ORGANISM: human

<400> SEQUENCE: 6

Glu Ile Ser Ala Pro Ser Asn Phe Glu His Arg Val His Thr Gly Phe
1               5                   10                  15

Asp Gln His Glu Gln
                20
```

```
<210> SEQ ID NO 7
<211> LENGTH: 21
<212> TYPE: PRT
<213> ORGANISM: human;

<400> SEQUENCE: 7

Glu Ile Ser Pro Pro Ser Asp Phe Glu His Thr Ile His Val Gly Phe
1               5                   10                  15

Asp Ala Val Thr Gly
            20

<210> SEQ ID NO 8
<211> LENGTH: 18
<212> TYPE: PRT
<213> ORGANISM: yeast

<400> SEQUENCE: 8

Ile Ser Tyr Asn Ala Lys His Ile His His Val Gly Val Asp Ser Lys
1               5                   10                  15

Thr Gly

<210> SEQ ID NO 9
<211> LENGTH: 21
<212> TYPE: PRT
<213> ORGANISM: human

<400> SEQUENCE: 9

Asp Ile Gly Ala Pro Ser Gly Phe Lys His Val Ser His Val Gly Trp
1               5                   10                  15

Asp Pro Gln Asn Gly
            20

<210> SEQ ID NO 10
<211> LENGTH: 21
<212> TYPE: PRT
<213> ORGANISM: yeast

<400> SEQUENCE: 10

Gly Val Ser Ser Pro Thr Asn Phe Thr His Lys Val His Val Gly Phe
1               5                   10                  15

Asp Pro Glu Thr Gly
            20

<210> SEQ ID NO 11
<211> LENGTH: 8
<212> TYPE: PRT
<213> ORGANISM: human

<400> SEQUENCE: 11

Lys Lys Glu Leu Ile Ile Asn Glu
1               5

<210> SEQ ID NO 12
<211> LENGTH: 8
<212> TYPE: PRT
<213> ORGANISM: human

<400> SEQUENCE: 12

Val Gly Thr Pro Tyr Trp Met Ala
1               5

<210> SEQ ID NO 13
<211> LENGTH: 268
```

```
<212> TYPE: DNA
<213> ORGANISM: mouse

<400> SEQUENCE: 13
aagcagcagc ggcgcgagtt gctcttcaat gaggtggtga tcatgcggga ctaccggcac     60
gagaacgtgg tggagatgta caacagctac ctggtgggtg acgaactctg ggtcgtcatg    120
gagttcctgg aaggcggcgc cctcacggat attgtcaccc acaccaggat gaacgaggaa    180
cagatcgccg ccgtgtgcct ggctgtgctt caggcgctgg ctgtgctcca cgcccagggt    240
gtcatccaca gcgacataaa aacggaca                                       268

<210> SEQ ID NO 14
<211> LENGTH: 89
<212> TYPE: PRT
<213> ORGANISM: mouse

<400> SEQUENCE: 14

Lys Gln Gln Arg Arg Glu Leu Leu Phe Asn Glu Val Val Ile Met Arg
1               5                   10                  15

Asp Tyr Arg His Glu Asn Val Val Glu Met Tyr Asn Ser Tyr Leu Val
            20                  25                  30

Gly Asp Glu Leu Trp Val Val Met Glu Phe Leu Glu Gly Gly Ala Leu
        35                  40                  45

Thr Asp Ile Val Thr His Thr Arg Met Asn Glu Glu Gln Ile Ala Ala
    50                  55                  60

Val Cys Leu Ala Val Leu Gln Ala Leu Ala Val Leu His Ala Gln Gly
65                  70                  75                  80

Val Ile His Ser Asp Ile Lys Thr Asp
                85

<210> SEQ ID NO 15
<211> LENGTH: 489
<212> TYPE: DNA
<213> ORGANISM: mouse
<220> FEATURE:
<221> NAME/KEY: misc_feature
<222> LOCATION: (410)..(410)
<223> OTHER INFORMATION: unkown nucleotide

<400> SEQUENCE: 15
acctggtggg tgacgaactc tgggtcgtca tggagttcct ggaaggcggc gccctcacgg     60
atattgtcac ccacaccagg taccataggg cagcctgctg gctcatgtgc tccctggggt    120
ggaactggga ccctttaggc tctggtgata gacaagtgcc ctccagagtg tgggtggggc    180
agtgaggcca ggcacacagg atgggggtca tagcatcgtg gctccctgac ccctgttgag    240
gcgggtcttt gtgacctctt gttgtctaaa gcagggtagg ggcctcttca ctgcccactc    300
tcaccccagg gtgggatgcc caaggcagcg ctgagtgccc agttgctcct ctgcccgcgc    360
aggatgaacg aggaacagat cgccgcccgt gtgcctggct tgtgcttcan cgctggcttt    420
gtgctccacg cccagggtgt catccaccgt gacatcaaga gtgactctat cttgctgacc    480
catgatggc                                                            489

<210> SEQ ID NO 16
<211> LENGTH: 6
<212> TYPE: PRT
<213> ORGANISM: mouse

<400> SEQUENCE: 16
```

```
Gly Glu Gly Ser Thr Gly
1               5

<210> SEQ ID NO 17
<211> LENGTH: 6
<212> TYPE: PRT
<213> ORGANISM: mouse

<400> SEQUENCE: 17

Ser Leu Val Gly Thr Pro
1               5
```

PAK4, A NOVEL GENE ENCODING A SERINE/THREONINE KINASE

This application is a continuation of PCT International Application No. PCT/US99/11341, filed May 21, 1999, designating the United States of America, which is a continuation-in-part and claims priority of U.S. Ser. No. 09/082,737, filed May 21, 1998 now U.S. Pat. No. 6,013,500 issued Jan. 11, 2002, the contents of which are hereby incorporated by reference into the present application.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

The GTPases Rac and Cdc42Hs control diverse cellular functions. In addition to being mediators of intracellular signaling cascades, they have important roles in cell morphogenesis and mitogenesis. A novel PAK related kinase, PAK4, has been identified as a new effector molecule for Cdc42Hs. PAK4 interacts only with the activated form of Cdc42Hs through its GTPase binding domain (GBD). Co-expression of PAK4 and the constitutively active Cdc42HsV12 cause the re-distribution of PAK4 to the Brefeldin A sensitive compartment of the Golgi membrane and the subsequent induction of filopodia and actin polymerization. Importantly, the reorganization of the actin cytoskeleton was dependent on PAK4 kinase activity and on its interaction with Cdc42Hs. Thus, unlike other members of the PAK family, PAK4 provides a novel link between Cdc42Hs and the actin cytoskeleton. The cellular locations of PAK4 and Cdc42Hs suggests a role for the Golgi in cell morphogenesis.

Members of the Rho family of small GTPases Rac and Cdc42Hs have been implicated in diverse biological processes. These include roles in cell proliferation, progression through the cell cycle, and oncogenic transformation (Van Aelst and D'Souza-Schorey, 1997). Cdc42Hs and Rac also play important roles in signal transduction cascades such as those that lead to activation of both the JNK and the p38 families of MAP kinases, and thus lead to long term changes in gene expression (Bagrodia et al., 1995; Brown et al., 1996; Coso et al., 1995; Minden et al., 1995; Zhang et al., 1995). One of the most important functions of Rac and Cdc42Hs is the regulation of the organization of the actin cytoskeleton. Microinjection of Cdc42Hs into fibroblasts and a variety of other cell types causes the induction of filopodia protrusions followed by the formation of lamellipodia. While the induction of filopodia is caused by Cdc42Hs activation, the induction of lamellipodia is probably due to the ability of Cdc42Hs to activate Rac. Thus, co-expression of Cdc42Hs with a dominant negative Rac mutant results in the sustained induction of filopodia without the subsequent induction of lamellipodia. Furthermore, microinjection of activated Rac leads to the induction of lamellipodia, but not filopodia. In addition to the formation of polymerized actin structures, both Cdc42Hs and Rac induce the formation of focal complexes that are associated with the filopodia and lamellipodia. Finally, in some cells, both Cdc42Hs and Rac have been shown to have a role in the dissolution of stress fibers, which may be due to antagonism between these GTPases and a third GTPase, RhoA.

A great deal of effort has been made to identify the downstream molecular targets for Rac and Cdc42Hs. Several proteins were shown to interact with the activated forms of Rac and Cdc42Hs including PAK65, p67-phox, WASP, IQGAP, and MLK3 (Manser et al. 1994, Martin et al. 1995; Bagrodia et al.; 1995, Aspenstrom et al., 1996; Rana et al., 1996; Symons et al., 1996; Hart et al. 1996; Kuroda et al. 1996; Teramoto et al., 1996; Burbelo et al. 1995; Van Aelst et al., 1996). PAK was the first protein kinase that was shown to be a target for Rac and Cdc42Hs, and consequently drew much attention. Activated Rac and Cdc42Hs stimulate PAK autophosphorylation and stimulate its kinase activity. Several PAK family members have been identified and all were shown to interact with GTP bound forms of Rac and Cdc42Hs. These include human PAK1 and 2, mouse PAK3, and the rat homologues PAK $\alpha$, $\beta$, and $\gamma$ (Brown et al., 1996; Manser et al., 1994; Martin et al., 1995; Bagrodia et al.; 1995). The PAKs are all similar in structure, containing an amino terminal regulatory domain and a carboxyl terminal kinase domain. They are also all quite similar in sequence, exhibiting 73% overall sequence identity and approximately 92% sequence identity within the kinase domain (Sells and Chernof, 1997). The regulatory domains of the PAKs contain a GTPase binding domain GBD (Symons et al., 1996) (known also as Cdc42Hs/Rac Interactive Binding (CRIB) domain) (Burbelo et al., 1995) that is necessary and essential for their direct interaction with both Cdc42Hs and Rac.

The functions of the PAKs are not yet entirely known. The sequence similarities between the PAKs and yeast STE20, however, suggests a role in transcription activation or cell morphogenesis. In *Saccharomyces cerevisiae*, STE20 is activated by Cdc42p, and is an important component of the KSS/FUS3 MAP Kinase pathway. STE20 and the related CLA4 may also mediate cytoskeletal changes induced by Cdc42p, such as those that occur during cytokinesis. Because of the evolutionary conservation between many yeast and mammalian signaling enzymes, it seems likely that the PAKs may have functions similar to the yeast STE20 and CLA4 proteins. In fact, the PAKs have been shown to weakly activate the JNK MAP kinase pathway in some cells (Bagrodia et al., 1995; Brown et al., 1996; Zhang et al., 1995). This suggests that, like STE20, the PAKs may be involved in MAP Kinase pathways. Some groups have shown however, that the PAKs are not necessary for JNK activation, and thus their roles in MAP Kinase pathways are as yet unclear. The PAKs may also be involved in cytoskeletal organization. PAK1 was reported to induce filopodia and membrane ruffles similar to those induced by Cdc42Hs and Rac, and to localize to polymerized actin. Interestingly however, these cytoskeletal changes are partly independent of PAK1's kinase activity, and they also occur independently of PAK1's ability to bind the Rho GTPases. Thus, while overexpressed PAK1 can promote cytoskeletal changes, it may not specifically mediate the cytoskeletal changes induced by Rac and Cdc42Hs. Others have found that PAK1 does not induce filopodia or lamellipodia but instead has a role in the dissolution of stress fibers and down-regulation of focal adhesions. Finally, effector mutants of Rac and Cdc42Hs, (such as RacL61(Y40C) and Cdc42HsL61 (Y40C)) that do not bind the PAKs, maintain the ability to induce lamellopodia and filopodia. Taken together, these results suggest that the induction of lamellipodia and filopodia by Rac and Cdc42Hs can occur independently of the known PAKs.

Here the cloning and characterization of a novel serine/threonine kinase, PAK4 is reported. Like other members of the PAK family, PAK4 contains an amino terminal regulatory domain and a carboxyl terminal kinase domain. The kinase domain of PAK4 shares 53% sequence identity with those of the other PAKs. Outside of this region however, PAK4 is entirely different in sequence from the other PAKs, except for a short stretch containing a modified GBD motif. PAK4 is the first member of the PAK family to be identified that differs significantly in sequence from the other PAKs, and thus represents an entirely new member of the PAK family. PAK4 interacts specifically with the GTP bound form of Cdc42Hs via its GBD motif and weakly activates the JNK family of MAP kinases. Co-expression of PAK4 with Cdc42Hs causes PAK4 to translocate from a diffuse perinuclear area to the Golgi membrane and subsequently induced the formation of filopodia and actin polymerization. Thus, the Golgi translocation of PAK4 by Cdc42Hs may be important for its ability to induce filopodia. Furthermore, PAK4 interacts with the Cdc42Hs effector mutant, Cdc42HsL61(Y40C) that was previously was shown to induce filopodia independently of PAKs. These results indicate therefore, that PAK4, rather than the previously identified PAKs, provides a link between Cdc42Hs and the actin cytoskeleton.

SUMMARY OF THE INVENTION

This invention provides an isolated mammalian nucleic acid molecule encoding a PAK4 serine/threonine kinase.

This invention provides an isolated nucleic acid molecule encoding a mutant homolog of the mammalian PAK4 serine/threonine kinase whose amino acid sequence is set forth in FIG. 1A (SEQ ID NO: 2).

This invention provides a fusion protein comprising a PAK4 serine/threonine kinase or a fragment thereof and a second peptide.

This invention provides a purified mammalian PAK4 serine/threonine kinase.

This invention provides a protein comprising substantially the amino acid sequence set forth in FIG. 1A.

This invention provides a monoclonal antibody directed to an epitope of a PAK4 serine/threonine kinase.

This invention provides a method of inhibiting PAK4 function comprising administering a ligand comprising an amino acid domain which binds to a GTP binding protein so as to inhibit binding of the GTP binding protein to PAK4.

This invention provides a method of inhibiting PAK4 function comprising administering a ligand which binds to the GTP binding domain of PAK4 so as to inhibit PAK4 binding to a GTP binding protein.

This invention provides a method of inhibiting PAK4 serine/threonine kinase function comprising administering a ligand which blocks an ATP binding domain so as to inhibit PAK4 serine/threonine kinase function.

This invention provides a method of inhibiting growth of a tumor cell comprising blocking Cdc42Hs by administering a ligand capable of binding to a Cdc42Hs binding site of a PAK4 serine/threonine kinase.

BRIEF DESCRIPTION OF THE FIGURES

FIGS. 1A–1E. Sequence and expression pattern of PAK4.

FIGS. 1A–1B Nucleotide sequence of PAK4, a novel serine/threonine kinase (SEQ ID NO: 1 and SEQ OD NO: 2). The CRIB domain (amino acids 1–30) and the kinase domain (amino acids 323–574) are underlined. FIG. 1C. Alignment of the kinase domain of PAK4 with those of PAK2 and STE20 (SEQ ID NO: 3, SEQ ID NO: 4 and SEQ ID NO: 5, respectively). FIG. 1D. Alignment of the GBD/CRIB motif of PAK4 (SEQ ID NO: 6) with the corresponding regions of several other mammalian (PAK2 (SEQ ID NO: 7) and WASP (SEQ ID NO: 9)) and yeast (STE20 (SEQ ID NO: 8) and CLA4 (SEQ ID NO: 10)) Rac and Cdc42Hs interacting proteins. FIG. 1E. Northern blot analysis of PAK4. A Northern blot containing mRNA from various human tissues was probed with a cDNA containing the kinase domain of PAK4. A band of approximately 3 KB is indicated.

FIG. 2A. Recombinant PAK4 and hPAK2 (2–3 µg) were analyzed by the overlay assay and probed with the indicated GTPase preloaded with either $[\gamma^{32}P]GTP$ or $^{32}[\beta P]GDP$ as described in materials and methods. FIG. 2B. Cos-1 cells were transiently transfected with expression vectors containing HA tagged PAK4 or PAK4ΔGBD, (a deletion mutant lacking the GBD/CRIB domain). After transient expression, Cos-1 cells were harvested, immunopurified with the anti HA antibodies, separated by SDS PAGE and transferred to nylon membranes. Binding of PAK4 or PAK4DGBD to $[\gamma^{32}P]GTP$ loaded Cdc42Hs was assessed as in FIG. 2A. To ensure that both wild-type PAK4 and PAK4AGBD were expressed at approximately equivalent levels, cell extract (25 µg) was analyzed by Western Blots probed with anti HA antibody.

FIGS. 3A–3B. Analysis of PAK4 kinase activity.

FIG. 3A. NIH3T3 cells were transfected with either empty Srα vector (control) or with increasing doses of Srα expression vectors containing the PAK cDNA fused to an HA epitope tag (0.5 and 1 µg). After transient expression, PAK4 was immunopurified from cell lysates using anti HA antibody. Immunopurified PAK4 was incubated with Histone H4, or without any substrate in the presence of $[\gamma-^{32}P]ATP$ and kinase buffer (Minden et al., 1994). Substrate phosphorylation was analyzed after SDS PAGE and autoradiography. Autophosphorylation of the 70 kD PAK4 and a band of approximately 43 kDa that co-purifies with PAK4 is indicated. FIG. 3B. Cos-1 cells were transfected with 1 µg of expression vectors containing either wild-type PAK4 or the indicated PAK4 mutants, all fused to HA tags. After transient expression, immunopurified PAK4 was used to phosphorylate Histone H4 in the presence of kinase buffer and $[\gamma-^{32}P]ATP$. Substrate phosphorylation is indicated. Similar results were obtained with NIH3T3 cells. FIGS. 3C–3E. NIH3T3 cells were transfected with empty Srα vector (control) or increasing doses of Srα myc tagged PAK4 expression vector (0.2, 0.6, or 1 µg) together with 1 µg of HA tagged JNK, ERK, or p38 expression vectors. As positive controls, cells were either transfected with expression vectors for Rac2L61 or RasV12 or treated with 400 mM sorbitol, as indicated. After transient expression, JNK, ERK, or p38 were immunopurified from cell lysates using anti HA antibody. Immunopurified proteins were incubated in kinase buffer and $[\gamma-^{32}P]ATP$ together with either GST-cJun, GST-ATF2, or MBP as substrates, respectively (Minden et al., 1995). Substrate phosphorylation was visualized after SDS PAGE and autoradiography. Substrate phosphorylation was quantitated by phosphorimager analysis. The numbers indicated are the averages of three independent experiments.

FIGS. 4A–4J. Localization of PAK4 and its effects on the actin cytoskeleton.

FIGS. 4A–4F. Porcine endothelial cells (PAE) were microinjected with HA tagged PAK4 expression vector alone or in combination with Myc tagged Cdc42HsV12 or RacV12 expression vectors (50 ng/μl plasmid). Cell were fixed 11–14 hours after injection and PAK4 was visualized by immunofluorescence microscopy after staining with FITC tagged HA antibody. Polymerized actin was visualized after staining with Rhodamine conjugated phalloidin. FIGS. 4G–4J. PAE cells were microinjected with Myc tagged PAK2 expression vector alone and in combination with Cdc42HsV12 or RacV12 expression vectors. Polymerized actin was visualized as described in FIGS. 4A–4F. Arrows indicate the injected cells.

FIGS. 5A–5H PAK4 is recruited by Cdc42Hs to the BFA sensitive compartment of the Golgi.

PAE cells were microinjected with HA tagged PAK4 expression vector alone or in combination with Cdc42HsV12 expression vector. After 12–16 hours cells were either left untreated or treated with 5 μg/ml BFA for 3–5 min. at 37° C. followed immediately by fixation. b-COP was visualized by a specific antibody against b-COP protein (Gift of Richard Khan). To compare the localization of PAK4 to b-COP compare fluorescence micrograph of anti HA staining to that of anti b-COP staining.

FIGS. 6A–6H. PAK4 localization to the Golgi and kinase activity are essential for actin polymerization.

Fluorescence micrographs of PAE cells microinjected with expression vectors containing HA tagged kinase inactive PAK4(M430) or the PAK4(E474) mutant, alone or in combination with Cdc42HsV12 expression vector. PAK4 was detected by HA antibody and polymerized actin was visualized by phalloidin staining.

Figure 7A:
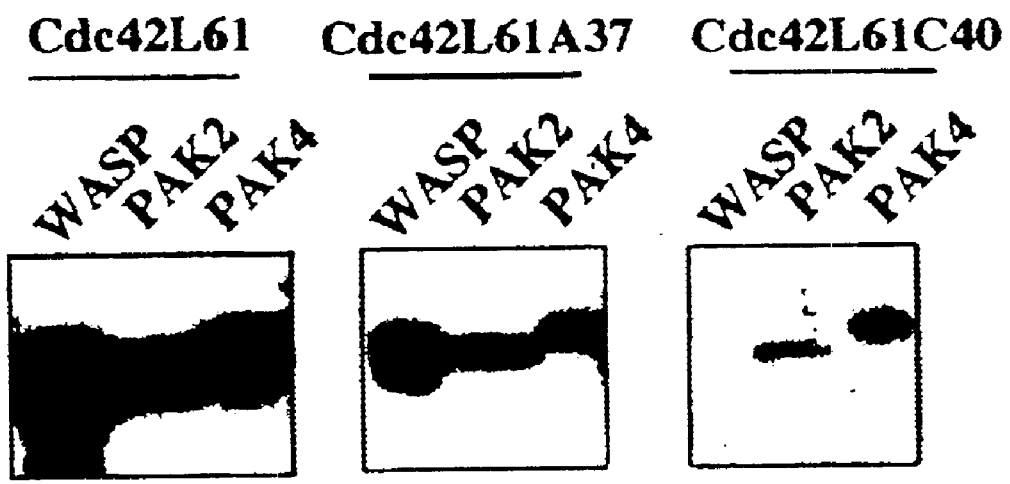
Figure 7B:
Figure 7C:
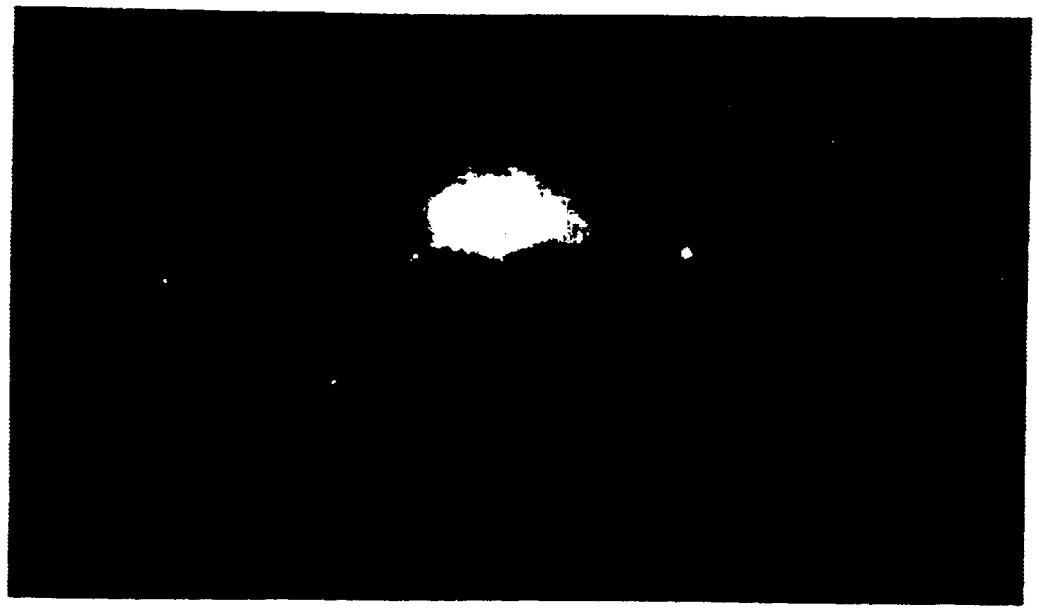

FIGS. 7A–7C. Analysis of Cdc42Hs effector mutants.

FIG. 7A. Recombinant PAK4, hPAK2, and WASP (2–3 μg) were analyzed by the overlay assay and probed with the indicated Cdc42Hs mutant preloaded with [$\gamma^{32}$P]GTP (Martin et al., 1995). FIGS. 7B–7C. Porcine endothelial cells (PAE) were injected with HA tagged PAK4 expression vector alone or in combination with Myc tagged Cdc42HsL61(C40) mutant. (100 ng/μl plasmid). Cell were fixed 11–14 hours after injection and PAK4 was visualized by immunofluorescence microscopy after staining with FITC tagged HA antibody.

FIGS. 8A–8C FIG. 8A. Partial cDNA of the mouse PAK4 (SEQ ID NO: 13). FIG. 8B. Predicted amino acid sequence of the partial mouse PAK4 cDNA (SEQ ID NO: 14). FIG. 8C. Partial genomic sequence of mouse PAK4 (SEQ ID NO: 15).

DETAILED DESCRIPTION OF THE INVENTION

The following standard abbreviations are used throughout the specification to indicate specific nucleotides:

C=cytosine A=adenosine
T=thymidine G=guanosine

This invention provides an isolated nucleic acid molecule encoding a PAK4 serine/threonine kinase. In an embodiment the isolated nucleic acid molecule encoding a PAK4 serine/threonine kinase is a DNA molecule. In another embodiment the isolated nucleic acid molecule encoding a PAK4 serine/threonine kinase is a cDNA molecule. In a further embodiment the isolated DNA molecule encoding a PAK4 serine/threonine kinase is a genomic DNA molecule. In an embodiment the isolated nucleic acid molecule encoding a PAK4 serine/threonine kinase is an RNA molecule.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide, PAK4 serine/threonine kinase, and as products for the large scale synthesis of the polypeptide (PAK4 serine/threonine kinase) by a variety of recombinant techniques. The molecule is useful for generating new cloning and expression vectors, transformed and transfected prokaryotic and eukaryotic host cells, and new and useful methods for cultured growth of such host cells capable of expression of the polypeptide (PAK4 serine/threonine kinase) and related products.

In another embodiment of the isolated nucleic acid molecule encoding a PAK4 serine/threonine kinase, the nucleic acid molecule encodes a mammalian PAK4 serine/threonine kinase. In a preferred embodiment of the isolated nucleic acid molecule encoding a PAK4 serine/threonine kinase, the mammalian PAK4 serine/threonine kinase is a human, mouse or rat PAK4 serine/threonine kinase. In a further embodiment of the isolated nucleic acid molecule encoding a mammalian PAK4 serine/threonine kinase, the nucleic acid molecule encodes a PAK4 serine/threonine kinase comprising an amino acid sequence as set forth in FIG. 1A (SEQ ID NO: 2). In an embodiment of the isolated nucleic acid molecule encoding a PAK4 serine/threonine kinase comprising an amino acid sequence as set forth in FIG. 1A (SEQ ID NO: 2), the encoded amino acid sequence comprises a GTPase binding domain (GBD). In another embodiment of the isolated nucleic acid molecule encoding the mammalian PAK4 serine/threonine kinase, the PAK4 serine/threonine kinase has substantially the same amino acid sequence as set forth in FIG. 1A (SEQ ID NO: 2).

In a further embodiment of the isolated nucleic acid molecule encoding the mammalian PAK4 serine/threonine kinase, the encoded PAK4 serine/threonine kinase has the amino acid sequence as set forth in FIG. 1A (SEQ ID NO: 2).

This invention provides an isolated nucleic acid molecule encoding a mutant homolog of the mammalian PAK4 serine/threonine kinase whose amino acid sequence is set forth in FIG. 1A (SEQ ID NO: 2). In an embodiment the isolated nucleic acid molecule encoding the above-described mutant homolog of the mammalian PAK4 serine/threonine kinase is a deletion mutant. In a further embodiment of the deletion mutant, the encoded mutant homolog comprises a GTPase binding domain. In a still further embodiment of the deletion mutant, the encoded mutant homolog does not comprise a GTPase binding domain. In an embodiment of the isolated nucleic acid molecule encoding the mammalian PAK4 serine/threonine kinase, the mammalian PAK4 serine/threonine kinase comprises the nucleic acid sequence set forth in FIG. 1A (SEQ ID NO:1).

This invention provides a fusion protein comprising a PAK4 serine/threonine kinase or a fragment thereof and a second peptide. Fusion of a peptide with a smaller peptide, for example, a tag such as a hemaglutinin (HA) or myc tag, is well known to one of ordinary skill in the art.

This invention provides a vector comprising the mammalian nucleic acid molecule encoding a PAK4 serine/threonine kinase. In an embodiment the vector is adapted for expression in a host cell which comprises the regulatory elements necessary for expression of the nucleic acid molecule in the host cell operatively linked to the nucleic acid molecule encoding the PAK4 serine/threonine kinase as to permit expression of the PAK4 serine/threonine kinase. In another embodiment of the vector, the host cell is a eukaryotic, bacterial, insect or yeast cell. In a further embodiment of the vector, the eukaryotic host cell is a mammalian cell. In a still further embodiment the vector is a plasmid.

This invention also provides a vector comprising the nucleic acid molecule encoding a mammalian PAK4 serine/threonine kinase, wherein the nucleic acid molecule is a cDNA molecule. In an embodiment the vector is adapted for expression in a host cell which comprises the regulatory elements necessary for expression of the nucleic acid molecule in the host cell operatively linked to the nucleic acid molecule encoding the PAK4 serine/threonine kinase as to permit expression of the PAK4 serine/threonine kinase. In another embodiment of the vector, the host cell is a eukaryotic, bacterial, insect or yeast cell. In a further embodiment of the vector, the eukaryotic host cell is a mammalian cell. In a still further embodiment the vector is a plasmid.

In an embodiment, a full-length cDNA nucleic acid molecule encoding a human PAK4 serine/threonine kinase is inserted by subcloning into a SRα plasmid and the resulting plasmid is designated as SRαHAPAK4. Plasmid SRαHAPAK4 was deposited on May 21, 1998 with the American Type Culture Collection (ATCC), 10801 University Boulevard, Manassas, Va. 20110–2209, U.S.A. under the provisions of the Budapest Treaty for the International Recognition of the Deposit of Microorganisms for the Purposes of Patent Procedure. Plasmid SrαHAPAK4 was accorded ATCC Accession Number 209888.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk⁻ cells and COS cells. Mammalian cells may be transfected by methods well known in the art such as calcium phosphate precipitation, electroporation and microinjection.

One of ordinary skill in the art will easily obtain unique sequences from the cDNA cloned in the Srα plasmid. Such unique sequences may be used as probes to screen various mammalian cDNA libraries and genomic DNAs, e.g. mouse, rat and bovine, to obtain homologous nucleic acid sequences and to screen different cDNA tissue libraries to obtain isoforms of the obtained nucleic acid sequences. Nucleic acid probes from the cDNA cloned in the Srα plasmid may further be used to screen other human tissue cDNA libraries to obtain isoforms of the nucleic acid sequences encoding PAK4 serine/threonine kinase as well as to screen human genomic DNA to obtain the analogous nucleic acid sequences. The homologous nucleic acid sequences and isoforms may be used to produce the proteins encoded thereby.

This invention provides a plasmid comprising the nucleic acid molecule encoding a human PAK4 serine/threonine kinase designated SrαHAPAK4 (ATCC Accession No. 209888).

This invention provides a nucleic acid probe comprising a nucleic acid molecule of at least 15 nucleotides capable of specifically hybridizing with a unique sequence included within the sequence of an isolated nucleic acid molecule encoding a mammalian PAK4 serine/threonine kinase. The nucleic acid probe may hybridize to any of the above-described isolated full-length nucleic acid molecules encoding a mammalian PAK4 serine/threonine kinase or fragments thereof.

This invention provides a nucleic acid probe comprising a nucleic acid molecule of at least 15 nucleotides which is complementary to a sequence of the isolated nucleic acid molecule encoding a mammalian PAK4 serine/threonine kinase.

The nucleic acid probe is complementary to a sequence of any of the above-described isolated full-length nucleic acid molecules encoding a mammalian PAK4 serine/threonine kinase or fragments thereof.

This invention provides a method of producing a PAK4 serine/threonine kinase, which comprises growing a host cell comprising any of the above-described vectors under suitable conditions permitting production of the PAK4 serine/threonine kinase and recovering the PAK4 serine/threonine kinase so produced. In an embodiment the method further comprises purifying the recovered PAK4 serine/ threonine kinase.

This invention provides a method of producing a polypeptide having the biological activity of a protein encoded by the nucleic acid molecule encoding a PAK4 serine/threonine kinase which comprises growing the above-described host cells under suitable conditions permitting production of the polypeptide and recovering the polypeptide so produced. In another embodiment the method further comprises purifying the recovered polypeptide.

This invention provides a purified mammalian PAK4 serine/threonine kinase. In an embodiment the purified mammalian PAK4 serine/threonine kinase is a human PAK4 serine/threonine kinase.

This invention provides a protein comprising substantially the amino acid sequence set forth in FIG. 1A.

This invention provides an oligonucleotide comprising a nucleic acid molecule of at least 15 nucleotides capable of specifically hybridizing with a unique sequence included within the sequence of the isolated nucleic acid molecule encoding a mammalian PAK4 serine/threonine kinase. In an embodiment of the oligonucleotide the nucleic acid is DNA. In another embodiment of the oligonucleotide the nucleic acid is RNA.

This invention provides an antisense oligonucleotide comprising a sequence capable of specifically hybridizing with a unique sequence included within the MRNA molecule encoding a mammalian PAK4 serine/threonine kinase.

This invention provides an antisense oligonucleotide comprising a sequence capable of specifically hybridizing with a unique sequence included within the genomic DNA molecule encoding a mammalian PAK4 serine/threonine kinase. This invention provides an antibody capable of binding to the PAK4 serine/threonine kinase which may be a purified mammalian PAK4 serine/threonine kinase or a purified human PAK4 serine/threonine kinase. In an embodiment the antibody is a monoclonal antibody. In another embodiment the antibody is a polyclonal antibody.

This invention provides a monoclonal antibody directed to an epitope of a PAK4 serine/threonine kinase.

Polyclonal antibodies may be produced by injecting a host animal such as rabbit, rat, goat, mouse or other animal with the immunogen of this invention, e.g. a purified mammalian PAK4 serine/threonine kinase or a purified human PAK4 serine/threonine kinase. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual*, (Cold Spring Harbor Laboratories, Cold Spring Harbor, N.Y.: 1988) the contents of which are hereby incorporated by reference.

The monoclonal antibodies may be produced by immunizing for example, mice with an immunogen. The mice are inoculated intraperitoneally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256: 495–497. Available murine myeloma lines, such as those from the American Type Culture Collection (ATCC) 10801 University Boulevard, Manassas, Va. 20110–2209 USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention any of the above-described antibodies may be labeled with a detectable marker. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. A "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

This invention provides a method of inhibiting PAK4 function comprising administering a ligand comprising an amino acid domain which binds to a GTP binding protein so as to inhibit binding of the GTP binding protein to PAK4. As used herein, PAK4 is a PAK4 serine/threonine kinase. As used herein, PAK4 function is defined as an effector for Cdc42Hs which mediates induction of filopodia.

This invention provides a method of inhibiting PAK4 function comprising administering a ligand which binds to the GTP binding domain of PAK4 so as to inhibit PAK4 binding to a GTP binding protein.

This invention provides a method of inhibiting PAK4 serine/threonine kinase function comprising administering a ligand which blocks an ATP binding domain so as to inhibit PAK4 serine/threonine kinase function.

As used herein ligands comprising an amino acid domain which binds to a GTP binding protein, which binds to the GTP binding domain of PAK4, or which block an ATP binding domain are defined as an amino acid molecule or fragment thereof which has an amino acid sequence complementary to a GTP binding protein, GTP binding domain of PAK4, or an ATP binding domain, respectively.

In an embodiment of any of the above-described methods of inhibiting PAK4 function, the inhibition of PAK4 function thereby inhibits polymerization of actin cytoskeleton. As used herein any of the above-described methods may be used to inhibit tumor cell growth.

In an embodiment of the method of inhibiting PAK4 function comprising administering a ligand comprising an amino acid domain which binds to a GTP binding protein so as to inhibit binding of the GTP binding protein to PAK4 or the method of inhibiting PAK4 function comprising administering a ligand which binds to the GTP binding domain of PAK4 so as to inhibit PAK4 binding to a GTP binding protein, the GTP binding protein is Cdc42Hs or Rac. In an embodiment of either of these methods the method may further comprise inhibition of induction of filopodia. The ligand which inhibits PAK4 function may thus inhibit cytokine pathways, e.g. TNFA and growth factor pathways, e.g. epidermal growth factor (EGF).

In an embodiment of the method of inhibiting PAK4 function comprising administering a ligand which binds to the GTP binding domain of PAK4 so as to inhibit PAK4 binding to a GTP binding protein or the method of inhibiting PAK4 serine/threonine kinase function comprising administering a ligand which blocks an ATP binding domain so as to inhibit PAK4 serine/threonine kinase function, the ligand is an antibody capable of binding to the PAK4 serine/threonine kinase. In another embodiment of these methods the antibody is a monoclonal or a polyclonal antibody.

This invention provides a method of inhibiting growth of a tumor cell comprising blocking Cdc42Hs by administering a ligand capable of binding to a Cdc42Hs binding site of a PAK4 serine/threonine kinase. In an embodiment of the method, the tumor cell growth is inhibited in vivo or in vitro. In another embodiment of these methods the ligand is an antibody capable of binding to the PAK4 serine/threonine kinase. In a further embodiment of these methods the antibody is a monoclonal or a polyclonal antibody.

This invention provides a pharmaceutical composition comprising an amount of any of the above-described ligands, including, but not limited to any of following oligonucleotides: an oligonucleotide comprising a nucleic acid molecule of at least 15 nucleotides capable of specifically hybridizing with a unique sequence included within the sequence of the isolated nucleic acid molecule encoding a mammalian PAK4 serine/threonine kinase, said oligonucleotide being DNA or RNA; an antisense oligonucleotide comprising a sequence capable of specifically hybridizing with a unique sequence included within the mRNA molecule encoding a mammalian PAK4 serine/threonine kinase; or an antisense oligonucleotide comprising a sequence capable of specifically hybridizing with a unique sequence included within the genomic DNA molecule encoding a mammalian PAK4 serine/threonine kinase, effective to prevent overexpression of a PAK4 serine/threonine kinase and a pharmaceutically acceptable carrier capable of passing through a cell membrane.

This invention provides a pharmaceutical composition comprising an amount of any of the following antibodies: an antibody capable of binding to the PAK4 serine/threonine kinase which may be a purified mammalian PAK4 serine/threonine kinase or a purified human PAK4 serine/threonine kinase; said antibody being a monoclonal antibody or a polyclonal antibody; or a monoclonal antibody directed to an epitope of a PAK4 serine/threonine kinase effective to block binding of a PAK4 serine/threonine kinase to a GTP binding protein and a pharmaceutically acceptable carrier capable of passing through a cell membrane.

This invention provides a method of treating an abnormality in a subject, wherein the abnormality is alleviated by the inhibition of binding of a PAK4 serine/threonine kinase and a GTP binding protein which comprises administering to the subject an effective amount of any of the above-described pharmaceutical compositions effective to prevent overexpression of a PAK4 serine/threonine kinase, thereby treating the abnormality in the subject. In an embodiment, the GTP binding protein is Cdc42Hs or Rac. In an embodiment, the abnormality is cancer or arthritis.

This invention provides a method of treating an abnormality in a subject, wherein the abnormality is alleviated by the inhibition of binding of a PAK4 serine/threonine kinase and a GTP binding protein which comprises administering to the subject an effective amount of the pharmaceutical composition comprising any of the above-described antibodies effective to block binding of the PAK4 serine/threonine kinase and the GTP binding protein in the subject, thereby treating the abnormality in the subject. In an embodiment, the GTP binding protein is Cdc42Hs or Rac. In an embodiment, the abnormality is cancer or arthritis.

This invention provides a method of administering the above-described pharmaceutical composition comprising an amount of any of the above-described ligands, oligonucleotides or antibodies which are determined to be potentially therapeutic, wherein the administration is intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery.

The present invention also provides a pharmaceutical composition comprising a effective amount of any of the above-described ligands, oligonucleotides or antibodies which are determined to be potentially therapeutic and a pharmaceutically acceptable carrier. In the subject invention an "effective amount" is any amount of the above-described ligands, oligonucleotides or antibodies which are determined to be potentially therapeutic, which, when administered to a subject suffering from a disease or abnormality against which the above-described ligands, oligonucleotides or antibodies which are determined to be potentially therapeutic, are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The above-described ligands, oligonucleotides or antibodies which are determined to be potentially therapeutic can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The above-described ligands, oligonucleotides or antibodies which are determined to be potentially therapeutic can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular ligands, oligonucleotides or antibodies in use, the strength of the preparation, the mode of administration, and the advancement of the disease condition or abnormality. Additional factors depending on the particular subject being treated will result in a need to adjust dosages, including subject age, weight, gender, diet, and time of administration.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

FIRST SERIES OF EXPERIMENTS

MATERIALS AND METHODS

Isolation of PAK4

To isolate PAK4, a pair of degenerate oligonucleotide primers were synthesized based on the amino acid sequences conserved among the kinase domains of yeast STE20 and human PAK65. (The two oligos corresponded to the amino acid sequences "KKELIINE" (SEQ ID NO: 11) and "VGTPYWMA", respectively (SEQ ID NO: 12)). The two primers were used to generate a PCR product using Jurkat cell cDNA as a template. Low stringency conditions were used so that diverse products could be obtained. PCR products were gel purified and subcloned. Inserts were sequenced using the dideoxy chain termination method. A 400 bp PCR product containing significant homology to the catalytic domain of STE20 was used as a probe to screen both a human Jurkat cell cDNA library (in the ZAP ExpressTM EcoRI vector) and **a human fetal brain cDNA library (in XTriplEXTM vector). Nylon transfer filters containing $1 \times 10^6$ recombinant plaques were hybridized with the randomly primed [α-$^{32}$P] dCTP-labeled probe (Prime-It II kit, Stratagene) overnight at 42° C. in 6×SSC, 50% formamide, 0.1% SDS, and washed at 65° C. in 2×SSC, 0.1% SDS according to standard protocol. Positive plaques (≈40) were taken through further purification and excised in vivo as plasmids. The positive inserts were sequenced on both strands. 5' RACE was carried out to determine that the sequence upstream to the start codon contains an in frame stop codon.

Cell Culture and Transfection

All cells lines were grown at 37° C. in 5% $CO_2$ and cultured in Dulbecco's modified Eagle's medium (DMEM) media containing appropriate serum (HeLa, 10% fetal bovine serum (FBS) ; NIH3T3, 10% bovine calf serum (BCS) ; COS-1, 10% newborn calf serum (NCS)). All media were supplemented with 100 units/ml penicillin, 100 (μ/ml streptomycin, and 1 mM glutamate. Transient transfection assays were carried out using the lipofectamine (GIBCO BRL) method according to the manufacturer protocol.

Protein Kinase Assays

To assay kinase activity of PAK4, NIH3T3 cells were transfected with either empty Sra expression vector or expression vectors containing HA tagged PAK4. Cells were harvested in M2 buffer (Minden et al., 1994) 48 h after transfection. Approximately 100 μg of cell extracts were mixed with anti-HA antibody and protein A sepharose and incubated 2 h to overnight at 4° C. rotating. The immune complexes were washed two times with M2 buffer and two times in 20 mM HEPES, pH 7.5 and incubated in kinase buffer (described in (Minden et al., 1994)) containing, 20 μM ATP and 5 μCi of [γ-$^{32}$P]ATP either alone or together with 5 μg Histone H4 (Boehringer Mannheim) or no substrate, at 30° C. for 20 min. The reaction was stopped by boiling in 4×SDS loading buffer. Proteins were resolved by SDS-polyacrylamide gel electrophoresis (PAGE), and substrate phosphorylation and autophosphorylation were visualized by autoradiography. JNK, ERK, and p38 activity were measured as described (Minden et al., 1995).

Northern Blots

The Northern analysis was performed using a human tissue blot (Clontech). Hybridization and washes were carried out as recommended by the manufacturer. The probe was prepared by labeling a 400 bp cDNA fragment corresponding to the kinase domain of PAK4 with [α-$^{32}$-P] dCTP (Amersham International PLC) by random priming (Stratagene).

Overlay Assay

The overlay assay is described in Martin et al., 1995. Recombinant and immunopurified proteins were separated on SDS-PAGE followed by blotting to a PVDF membrane, washing, and blocking with PBS containing 1% BSA and 100 mM DTT. Recombinant GTPases (2–5 µg) were preloaded with the indicated radiolabeled nucleotide and were incubated for 5–8 min. with the PVDF filter. The filter was washed for 5 min. and was exposed to a film for 2 hours. Recombinant proteins were expressed and purified from Sf9 cells as previously described (Martin et al. 1995). Various Cdc42Hs effector mutants were prepared in E. coli as GST fusion proteins and were purified on a glutathione sepharose beads and eluted from the beads by 5 mM reduced glutathione.

Western Blot

25 µg of COS-1 cell lysates were resolved by SDS-PAGE and transferred to PVDF membrane. The membrane was blocked in PBS containing 0.2% Tween-20 (PBST) and 4% non-fat milk for 1 h and then incubated with anti HA antibody diluted in PBST containing 4% non-fat milk for 1 h. After washing 3 times with PBS, the membrane was probed with secondary antibody, peroxidase-conjugated goat IGG fraction to mouse IGG for 1 h. After washing 3 times with PBS, the immunocomplexes were visualized by enhanced chemiluminescence (ECL) reagent ECL (Amersham Corp.).

Microinjections and Immunofluorescence Microscopy

Microinjections and immunofluorescence microscopy was carried out essentially as described (Symons et al., 1996). Briefly, PAE cells were grown in DMEM medium containing 10% fetal bovine serum and were plated on a coverslip. Expression vectors encoding various PAK4, PAK2, Cdc42Hs and Rac mutants diluted to a concentration of 50 ng/µl in injection buffer (5 mM glutamate, 130 mM KCL), were microinjected into the nucleus of—100 of sub-confluent PAE cells. Injected cells were incubated for 16–20 hr. at 37° C. and fixed in 4% formaldehyde. Cells were permeabilized with PBS containing 0.1% Triton x-100 and incubated in the presence of the primary monoclonal antibodies anti HA or anti Myc for 60 min. The coverslips were washed with PBS containing 0.1% Triton x-100 and was incubated for 30 min. with the second antibody Texas Red conjugated anti mouse antibody. To visualized F-actin, cells were washed again and were incubated with FITC conjugated phalloidin. Fluorescence photomicroscopy was carried out on a Zeiss Axiophot with appropriate filters for fluorescence detection.

Preparation of Recombinant Proteins

To prepare recombinant PAK4, a BamH1/NOTI fragment containing the full length PAK4 was subcloned into the pAcO-3 baculovirus expression vector containing a 5' Glu-Glu tag. Recombinant protein was then prepared and purified as described in (Martin et al. 1995). Recombinant PAK2 was generated as described in (Martin et al. 1995).

Plasmids

To construct HA tagged PAK4, an EcoRI fragment of the cDNA was ligated in frame into the EcoRI site of Bluescript II KS(+) vector containing a 5' HA tag. HA-PAK4 was then removed from Bluescript II KS(+) as a HindIII/StuI fragment and subcloned into HindIII/SmaI site of expression vector SRα3 (Takebe et al., 1988). PAK4(M350), PAK4 (M474), and PAK4(E474) were generated by site directed mutagenesis (Stratagene QuickChange kit) of K(350) or S(474) to methionine or Aspartate. Rac2L61, JNK, p38, ERK and ERK are described in Minden et al., 1995.

RESULTS

Identification of PAK4, a Novel Member of the PAK Family

To identify new PAK related proteins, degenerate primers were designed corresponding to regions of homology between the kinase domains of yeast STE20 and mammalian hPAK2.

Figure 1E:
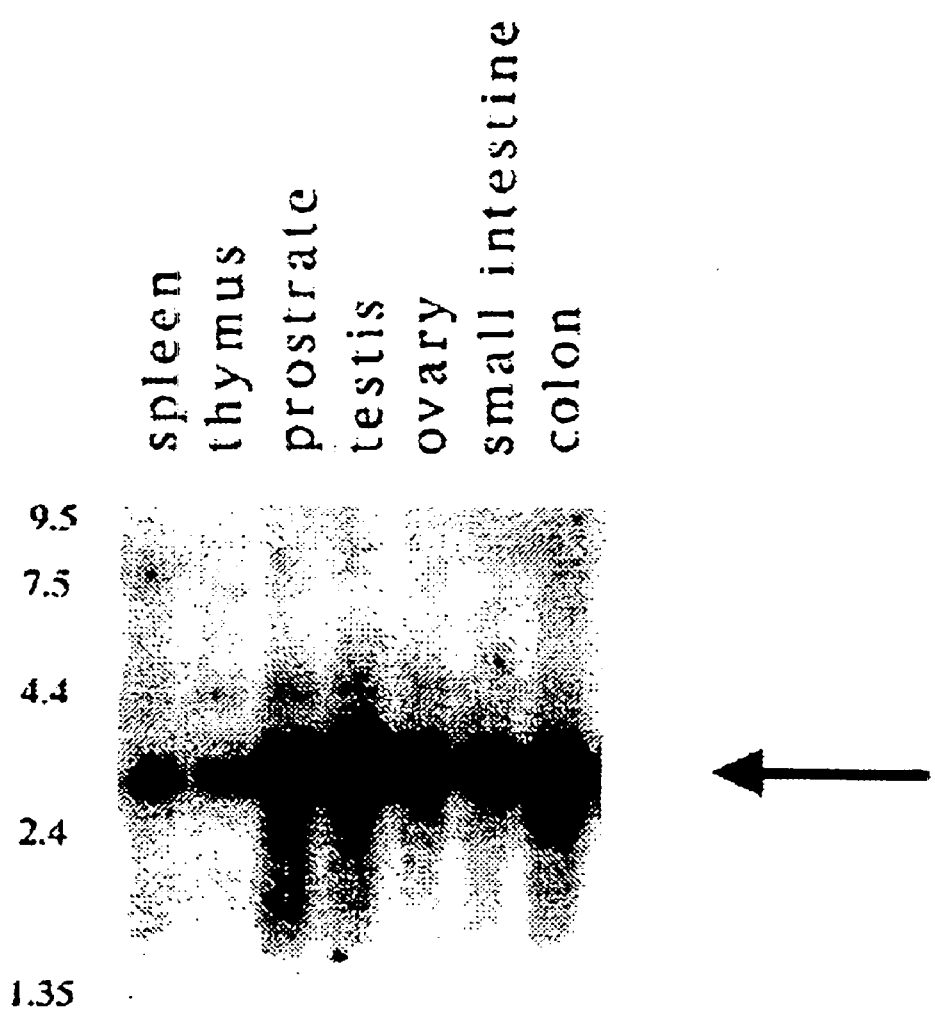

These primers were used to generate PCR products from Jurkat cell CDNA. The PCR products were subsequently sub-cloned and sequenced, and sequence homologies were obtained by Blast searches of the Gene Bank. Using this technique, partial sequences were identified for several novel putative protein kinases. One of the partial cDNAs was used as a probe to screen Jurkat cell and fetal brain cDNA libraries as described in materials and methods. Two identical clones that hybridize with this cDNA were isolated. One of the clones contained a complete open reading frame of approximately 1.7 KB as shown in Figures 1A–1B. Like the PAK family of kinases, the carboxyl terminal portion of the predicted protein sequence contains the 11 sub-domains that are characteristic of serine/threonine protein kinases. Blast searches of the Gene Bank confirmed that this region is most similar to the kinase domain of human PAK2. This putative kinase domain has 53% identity and 73% similarity with PAK2, and 49% identity and 71% similarity with yeast STE20 (FIG. 1C). The amino terminal putative regulatory domain of PAK4 does not share homology with any other known proteins except for a short sequence resembling a modified GBD/CRIB domain. This conserved sequence of approximately 16 amino acids is found in many proteins that bind Rac and Cdc42Hs (Burbelo et al., 1995). This sequence has been shown to be essential and necessary for interactions of these proteins with the GTPases (Burbelo et al., 1995). The GBD/CRIB domain found on PAK4 in comparison with those found on several other Cdc42Hs/Rac binding proteins is shown in FIG. 1D. To determine the expression profile of PAK4, a Northern blot was probed with a cDNA probe that corresponds to the kinase domain of PAK4. A band of approximately 3 KB was seen in all of the human tissues that were analyzed. PAK4 appears to be most highly expressed in prostate, testis, and colon (FIG. 1E). A band of the same size was detected when the Northern blot was probed with a cDNA corresponding to the PAK4 regulatory domain (not shown).

PAK4 Interacts with GTP Bound Form of Cdc42Hs

Figure 2A:
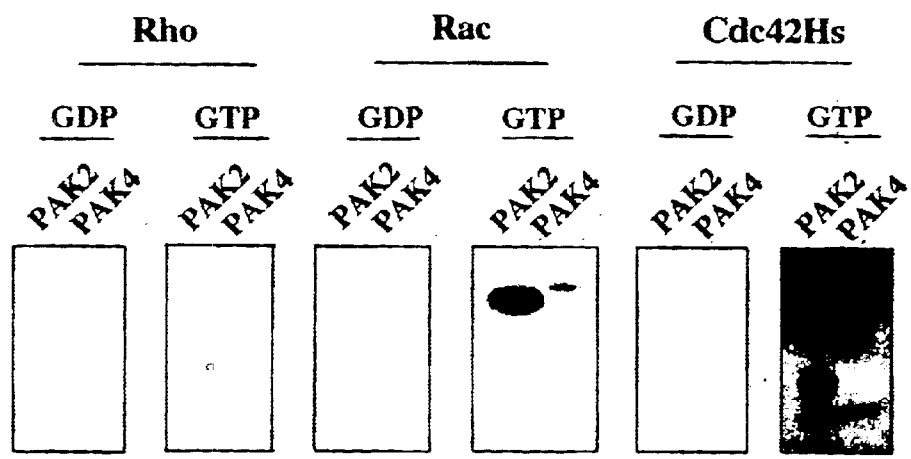
FIGS. 2A–2B. PAK4 interacts with the activated Cdc42Hs through its GBD/CRIB domain.
Figure 2B:
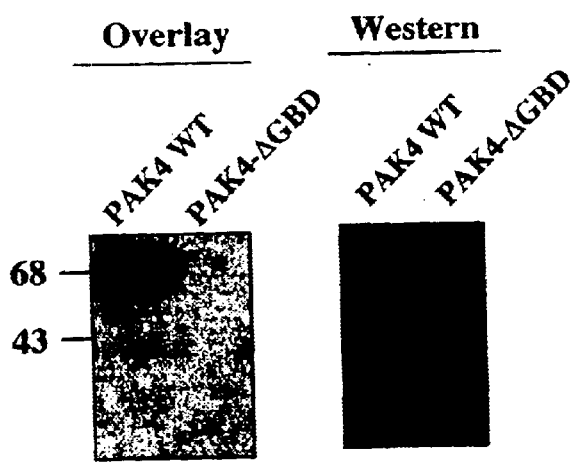
Figure 4A:
Figure 4B:
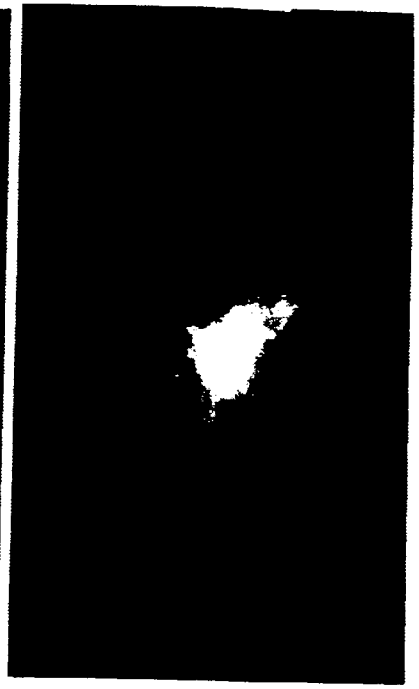
Figure 4C:
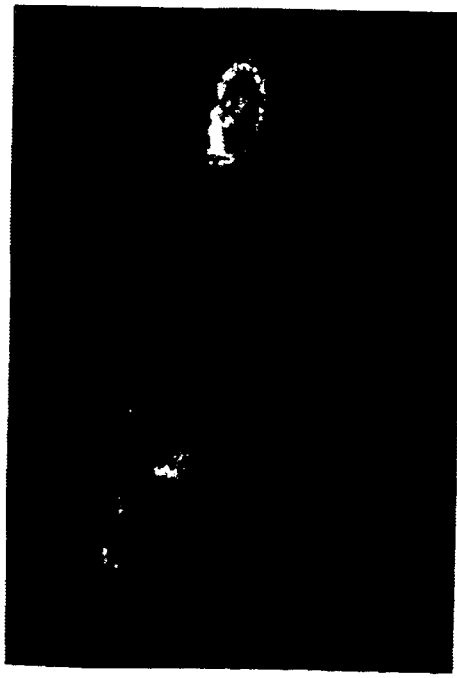
Figure 4D:
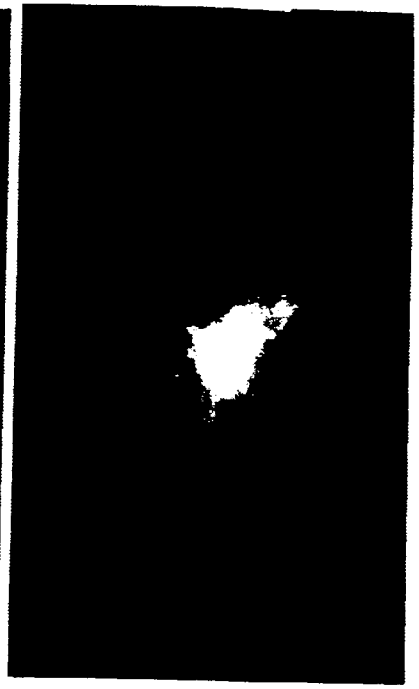
Figure 4H:
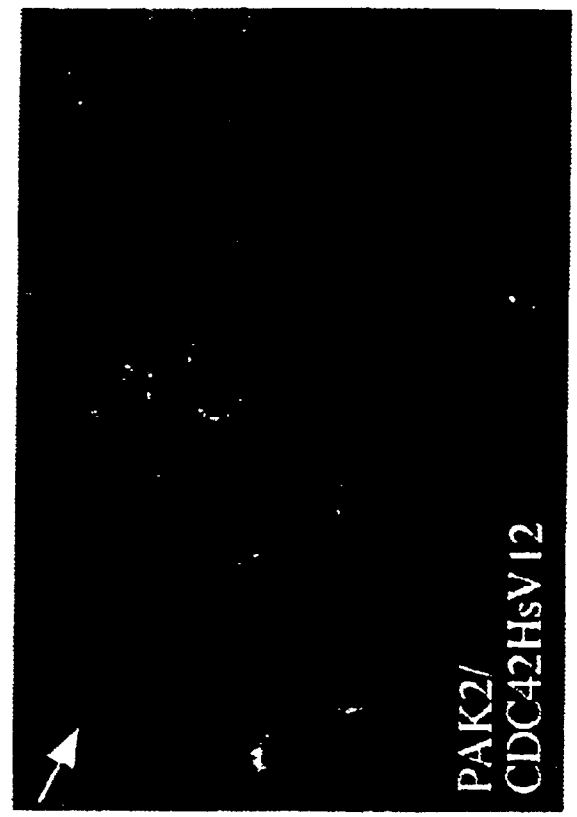
Figure 4G:
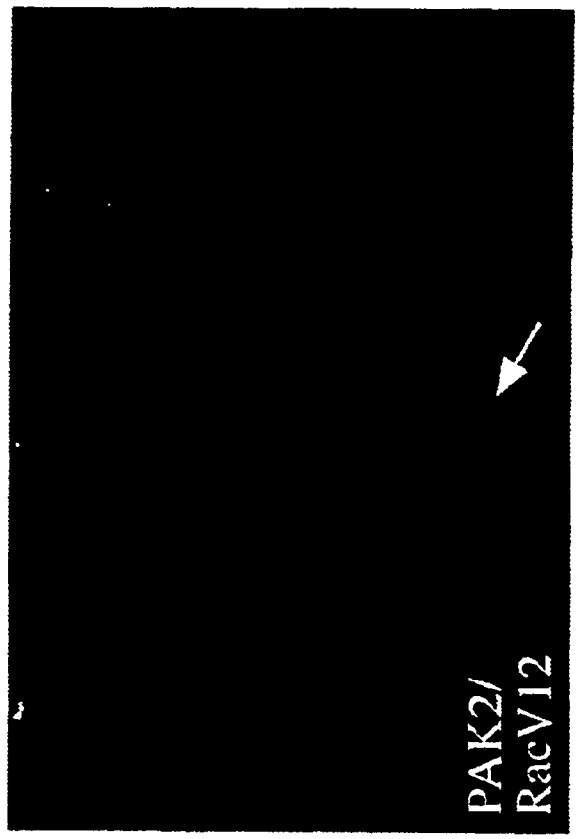
Figure 4J:
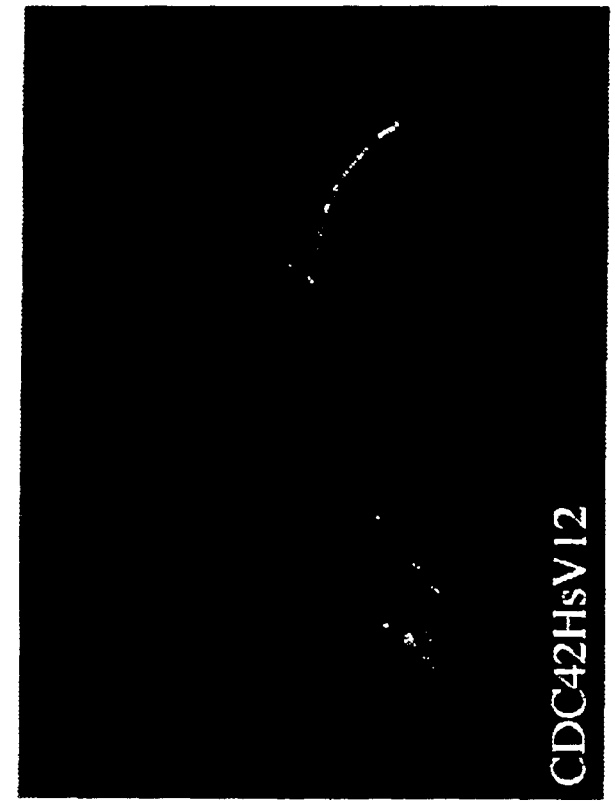
Figure 4I:
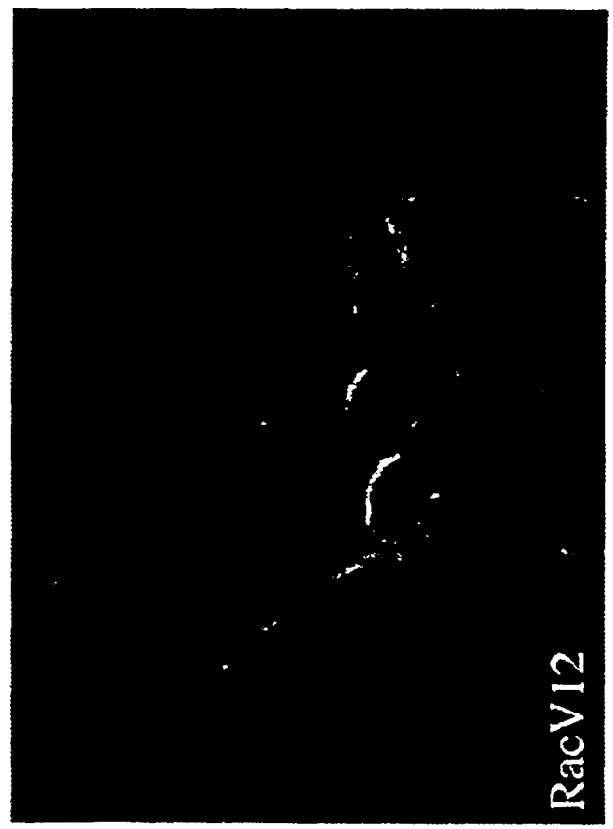

The finding that PAK4 has a putative GBD/CRIB motif suggests that it is a new target for Cdc42Hs and/or Rac. An overlay assay was used to determine whether PAK4 interacts with either of these GTP binding proteins. It was found that PAK4 interacts tightly with the GTP bound form of Cdc42Hs and not with the inactive GDP bound form of Cdc42Hs. A much weaker interaction was detected with the GTP bound form of Rac, and no binding was observed with Rho. In contrast, PAK2 interacts with similar affinity to the GTP bound forms of either Rac or Cdc42Hs (FIG. 2A). PAK4 lacking the GBD/CRIB domain (PAK4DGBD) does not bind to Cdc42Hs, indicating that the GBD/CRIB domain is required for binding (FIG. 2B).

PAK4 Autophosphorylates and Phosphorylates an Exogenous Substrate

The analysis of PAK4's kinase activity has revealed that it behaves similarly to other serine/threonine kinases.

NIH3T3 cells were transfected with either wild-type PAK4 or various mutants of PAK4. PAK4 was immunopurified from cell lysates and incubated in kinase buffer with g-$^{32}$P-ATP in the presence or absence of the substrate Histone H4. Substrate phosphorylation and autophosphorylation were analyzed after SDS-PAGE and autoradiography. The presence of a band of the exact same size as PAK4 strongly suggests that, like the other PAKs, PAK4 can autophosphorylate (FIG. 3A). PAK4 also co-immunopurified with a 42 kDa protein that became phosphorylated in the kinase assay, suggesting that it may be a substrate for PAK4 (FIG. 3A). Immunopurified PAK4 was also able to phosphorylate an exogenous substrate, Histone H4 (FIG. 3B). The activity of a PAK4(M350) mutant was also tested. This mutant contains a mutation in which the conserved lysine in subdomain II is converted to a non-phosphorylatable residue, methionine. Mutation of this conserved lysine disrupts the ATP binding site of nearly all serine/threonine kinases that have been analyzed (Hanks et al., 1988). Immunopurified PAK4 (M350) was completely unable to autophosphorylate or, as shown in FIG. 3B, to phosphorylate Histone H4. Most serine/threonine kinases contain a conserved serine or threonine residue within the linker region between kinase subdomains VII and VIII. This residue usually becomes phosphorylated either by autophosphorylation or by an upstream kinase. Phosphorylation of this residue is essential for the activities of most serine/threonine kinases (Johnson et al., 1996; Marshall, 1994; Pelech, 1996; Zhang et al., 1994). Consistent with this, mutation of the corresponding serine in PAK4 to a methionine results in a completely inactive PAK4 (M474) (FIG. 3B). Many protein kinases become further activated when the regulatory domain is removed. PAK4D which contains only the kinase domain was generated. PAK4D exhibits at least 5 fold more kinase activity than wild-ype PAK4, suggesting that the carboxyl terminal portion of PAK4 contains a regulatory domain (FIG. 3B). Like the wild-type protein however, mutation of the lysine in subdomain II to generate PAK4D(M350) results in a completely inactive kinase (FIG. 3B).

PAK4 Activates the JNK Pathway

One of the functions of Cdc42Hs and Rac is to activate the JNK and p38 MAP Kinase pathways (Bagrodia et al., 1995; Brown et al., 1996; Coso et al., 1995; Minden et al., 1995; Zhang et al., 1995). Since PAK4 is a target for Cdc42Hs, its ability to activate mammalian MAP Kinase pathways was tested. NIH3T3 cells were transfected with increasing doses of an expression vector containing the PAK4 cDNA. These were co-transfected with expression vectors containing epitope tagged JNK, ERK, or p38 cDNAs. After transient expression, JNK, ERK, or p38 were immunopurified from cell lysates using antibodies against the epitope tag, followed by an in vitro kinase assay. The results indicate that overexpression of the wild-type PAK4 leads to activation of the JNK pathway, although this activation is somewhat weak compared with other JNK activators such as Rac or Cdc42Hs (FIG. 3C). PAK4 has little activity towards ERK, and does not activate the p38 pathway (FIGS. 3D and E).

PAK4 induces localized actin polymerization and induces the formation of filopodia Since PAK4 is a novel target for Cdc42Hs, its role in the induction of cytoskeletal changes was studied. Microinjection of fibroblasts with purified constitutively active Cdc42HsV12 protein has been shown to lead to a transient induction of filopodia (Kozma et al., 1995; Nobes and Hall, 1995). The filopodia disappear within a short time (by 15–30 minutes) after microinjection of the protein followed by the formation of lamellipodia, due to the ability of Cdc42Hs to activate Rac (Kozma et al., 1995; Nobes and Hall, 1995). Another consequence of Cdc42Hs microinjection is the dissolution of stress fibers. To see whether PAK4 can potentiate the cytoskeletal effects triggered by the GTPases, PAE cells were microinjected with expression vectors for HA tagged PAK4 either alone or together with myc tagged Cdc42HsV12 or Rac1V12 expression vectors (Symons et al., 1996). The experiments described herein were also carried out with NIH3T3 fibroblasts, with similar results. As shown in FIGS. 4A–4F, when expressed alone, PAK4 was localized in a perinuclear area and did not affect the actin cytoskeleton. Cells microinjected with expression vectors for constitutively active Rac1V12 or Cdc42HsV12 alone induced extensive lamellipodia. Filopodia were not observed in the Cdc42Hs injected cells because cells were analyzed between 12–16 hours after microinjection. Interestingly, co-expression of PAK4 with Cdc42HsV12 caused dramatic changes in the actin cytoskeleton and re-distribution of PAK4. When co-injected with Cdc42HsV12, PAK4 became concentrated in one side of the nucleus in an area that resembles the trans Golgi compartment (FIGS. 4A–4F). Dual staining with phalloidin and HA antibody revealed a striking co-localization of PAK4 with polymerized actin clusters (FIGS. 4A–4F), and in cells expressing lower levels of PAK4, polymerized actin was detected around vesicles (data not shown). In addition, co-expression of PAK4 and Cdc42HsV12 induced the sustained formation of actin enriched filopodia protrusions in more than 70% of the injected cells and also caused the dis-assembly of stress fibers (FIGS. 4A–4F). Co-expression of PAK4 with a dominant negative Cdc42HsN17 had no effect on PAK4 localization or the reorganization of the actin cytoskeleton (data not shown). Co-expression of PAK4 and the constitutively active Rac1V12 resulted in a very similar phenotype to that observed with Rac1V12 alone. Rac1V12 induced the formation of lamellipodia and relocalization of a small percentage of PAK4 from the perinuclear area to the lamellipodia (FIGS. 4A–4F). To test whether these phenotypes are specific for PAK4, PAK2 expression vector with either Rac1V12 or Cdc42HsV12 expression vector was co-injected. PAK2 was localized in the cytosol and the nucleus and was not redistributed by Rac or Cdc42Hs (data not shown). In addition, cells co-expressing Rac1V12 or Cdc42HsV12 together with PAK2 had similar cytoskeletal phenotypes as cells expressing Rac1V12 or Cdc42Hs alone (FIGS. 4G–4J). This data strongly suggests that in contrast to PAK2, PAK4 is the effector for Cdc42Hs that leads to the induction of filopodia and actin polymerization.

PAK4 is Recruited to the Golgi Apparatus by Activated Cdc42Hs

PAK4 appears to be regulated by specific recruitment by Cdc42Hs to an area resembling the trans-Golgi. It is interesting to note that the endogenous Cdc42Hs was recently shown to be localized primarily at Golgi membranes, and to localize with the Golgi membrane coatomer protein b-COP (Erickson et al., 1996). In addition, a recently identified Cdc42Hs related protein was also localized to the Golgi structure (unpublished observation). To determine whether PAK4 also localizes to the Golgi, injected cells were co-stained with anti HA and anti b-COP antibody. As presented in FIGS. 5A–5H, in cells expressing PAK4 alone, PAK4 was localized to perinuclear areas and was not co-localized with b-COP. In cells co-expressing PAK4 and Cdc42HsV12 however, PAK4 was co-localized with b-COP in the Golgi.

The effects of the drug Brefeldin A (BFA) on PAK4 location were tested. Golgi coatomer proteins are normally redistributed when cells are exposed to BFA (Orci et al., 1991). Likewise, Cdc42Hs is redistributed from its Golgi location when cells are treated with BFA (Erickson et al., 1996). Interestingly, treatment of injected cells with BFA was found to also cause a rapid redistribution of PAK4 from the Golgi to the cytoplasm and the nucleus. This is nearly identical to the effects of BFA on b-COP in these cells (FIGS. 5A–5H). This data strongly suggests that in the presence of Cdc42Hs, PAK4 is localized at a BFA sensitive component of Golgi membranes. In addition, BFA treated cells contained less filopodia and polymerized actin. This data suggests that the localization of PAK4 by Cdc42Hs to the Golgi may play an important role in the reorganization of actin.

PAK4 Kinase Activity is Required for its Ability to Induce Localized Actin Polymerization and to Potentiate Filopodia Formation by Cdc42Hs The effect of PAK4 mutants on the formation of filopodia and actin polymerization was tested. The kinase inactive PAK4(M350) was microinjected into cells either alone or together with Cdc42HsV12. Like PAK4 wt, PAK4(M350) was localized in the perinuclear area and was recruited by Cdc42Hs to the BFA sensitive compartment of the Golgi (FIGS. 6A–6H). However, in contrast to PAK4 wt, PAK4 (M350) was unable to induce localized actin polymerization or the formation of filopodia, and did not lead to a reduction in stress fibers (FIGS. 6A–6H). A putative constitutively active PAK4 mutant was also generated. This mutant was generated by mutation of serine 474 (in the linker region between subdomains VII and VIII) to a glutamic acid. The resulting PAK(E474) mutant had a greatly enhanced autophosphorylation activity (data not shown). Mutation of this conserved site to a negatively charged amino acid has been found to generate constitutively active mutants of many serine/threonine kinases including the PAKs (Benner et al., 1995; Manser et al., 1997; Szczepanowska et al., 1997). When expressed alone, PAK4(E474) localized to similar areas as PAK4 wt and PAK4(M350), and did not have any effect on the actin cytoskeleton. Like PAK4 wt, PAK4(E474) was recruited specifically by Cdc42HsV12 to the Golgi and induced the formation of filopodia and polymerization of actin to the same extent as wild-type PAK4 (FIGS. 6A–6H). Taken together, these data indicate that PAK4's kinase activity is not necessary for the cellular localization of PAK4, but is essential for its effects on actin polymerization. The kinase activity of wild-type PAK4 appears to be sufficient to induce the cytoskeletal changes however, as the PAK4(E474) mutant had no enhanced effect on actin polymerization and filopodia formation. Furthermore, unlike results described for PAK1, constitutively active PAK4 did not induce cytoskeletal changes on its own, but maintained the requirement for recruitment by Cdc42Hs to the golgi.

PAK4 Binds Cdc42Hs Effector Mutants to Induce Filopodia and Actin Polymerization Two effector mutants of constitutively active Cdc42HsL61 were previously examined to assess the role of PAK and other effectors in filopodia formation (Lamarche et al., 1996). Both mutants had single amino acid substitutions in the effector loop. One mutant, Cdc42HsL61(Y40C) could not bind PAK or several other GBD/CRIB domain containing proteins. The other mutant, Cdc42HsL61(F37A), maintained the ability to bind PAK and other GBD/CRIB domain containing proteins. Interestingly, both effector mutants were equally efficient in the ability to induce filopodia when microinjected into fibroblasts together with dominant negative Rac (Lamarche et al., 1996). These results would tend to suggest that PAK binding to Cdc42Hs is not necessary for filopodia formation. To see whether Cdc42HsL61(Y40C) could be mediating its effects through PAK4, PAK4 binding to Cdc42HsL61 and to the two effector mutants was tested. For comparison PAK2 and another GBD/CRIB containing protein, WASP (Symons et al., 1996) were also analyzed. As shown in FIG. 7A, all three proteins bound to Cdc42HsL61. Likewise, as expected, they also all bound to Cdc42Hs (F37A), though with a slightly lower affinity. Surprisingly however, PAK4 bound Cdc42HsL61(Y40C) with a similar affinity as was detected with Cdc42HsL61(F37A), although WASP and PAK2 did not bind Cdc42HsL61(Y40C) efficiently. Moreover, when Cdc42HsL61(C40) was co-injected into PAE cells with PAK4, PAK4 was recruited to the Golgi area, induced actin polymerization, and promoted the formation of filopodia (see FIGS. 7B–7C) The results suggest a mechanism whereby the effector mutant Cdc42HsL61 (Y40C) can induce filopodia formation. Although it can not efficiently bind PAK2, this mutant maintains the ability to interact with PAK4. Importantly, it was found that PAK4, rather than the other known PAKs, is the important mediator of filopodia formation by Cdc42Hs.

DISCUSSION

PAK4 was identified as a novel member of the PAK family. Like the other PAKs, PAK4 contains a GBD/CRIB domain at the N-terminus and a kinase domain at the C-terminus. The overall sequence identity to other PAKs, however, is significantly different. Although the kinase domain of PAK4 is more similar in sequence to the kinase domains of PAK 1, 2, and 3 than to any other known proteins, it shares only 53% sequence identity. PAK4 exhibits no sequence homology in the regulatory domain outside the GBD/CRIB sequences. Even the GBD/CRIB motif is similar, but not identical, to the GBD/CRIB motif in the other PAKs. This suggests that PAK4 may have a different function than the known PAKs. It was shown that PAK4 interacts preferentially with the GTP bound form of Cdc42Hs and activates the JNK family of MAP Kinases. Moreover, microinjection of PAK4 and Cdc42Hs plasmids into different cell types demonstrates that PAK4 has a profound effect on the actin cytoskeleton. When co-injected with Cdc42Hs, PAK4 is recruited by Cdc42Hs to the brefeldin A sensitive compartment of the Golgi, and subsequently induces actin polymerization at the Golgi. Strikingly, PAK4 also greatly stimulates the induction of filopodia when it is co-injected with Cdc42Hs. In contrast to other PAKs, PAK4 kinase activity and its interaction with the activated Cdc42Hs are essential for the induction of this phenotype. In addition, PAK4 interacts with the Cdc42Hs effector mutant (Cdc42L61(C40)) which was previously shown to be important in the induction of filopodia but which failed to bind other PAKs (Lamarche et al., 1996). The data provides a novel link between Cdc42Hs, PAK4, and actin polymerization, and supports the idea that the Golgi apparatus plays a role in cytoskeletal re-organization.

The Rho family of GTPases play key roles in the control of cell morphology. By using microinjection techniques it was demonstrated that Cdc42Hs triggers the formation of microspikes and filopodia followed by activation of Rac, which leads to the formation of lamellipodia. A third GTPase, RhoA, is implicated in the formation of stress fibers. In addition, all three GTPases regulate the assembly of focal complexes. The cytoskeletal changes triggered by these GTPases play important roles in cell motility and division and in the maintenance of cell shape. The identification of molecular targets which mediate these cytoskeletal effects is therefore of great importance. Several proteins were shown to interact with the activated form of Cdc42Hs, however, the molecular effector that links Cdc42Hs to the formation of filopodia has not yet been identified. Recent experiments with various effector mutants of Cdc42Hs demonstrated that the cytoskeletal changes induced by Cdc42Hs are independent of PAK1, 2 or 3. In this report it has been shown that a novel PAK related protein, PAK4, interacts only with the GTP bound form of Cdc42Hs and not with other Rho members. The interaction between Cdc42Hs and PAK4 is essential for targeting PAK4 to the Golgi compartment and subsequently for the re-organization of the actin cytoskeleton. In contrast to PAK1, 2, and 3, the kinase activity of PAK4 is not regulated by Cdc42Hs (data not shown). Thus, it appears to be recruitment of PAK4 by Cdc42Hs, rather than stimulation of its kinase activity, which is important for actin polymerization and cytoskeletal changes. PAK4's kinase activity is necessary however, because a kinase inactive PAK4 mutant was re-localized to the Golgi by Cdc42Hs, but failed to reorganize the actin cytoskeleton. In addition to kinase activity, localization by Cdc42Hs is critical for PAK4 to induce actin polymerization and filopodia formation. Even a constitutively active PAK4 could not bypass the need for recruitment by Cdc42Hs to the Golgi. This mutant localized to the same area in the cell as wild-type PAK4, and only when it was recruited to the Golgi compartment by Cdc42Hs did induce the formation of filopodia and actin polymerization. These experiments strongly suggest that PAK4 mediates its biological effect by translocation to a specific site by Cdc42Hs and thereby bringing PAK4 to close proximity with a putative substrate.

This mechanism of activation of PAK4 is substantially different than the one proposed for other PAK members. PAK 1 was shown to be recruited to the focal complexes induced by Cdc42Hs, but the recruitment to these sites did not require a direct interaction with Cdc42Hs. Recently, it was demonstrated that PAK1 is recruited to the focal complexes by interacting with a novel GTP/GDP exchange factor PIX. A specific proline rich sequence on the PAK regulatory domain interacts with the SH3 domain of PIX. Furthermore, it was proposed that the PAK/PIX complex activates the Rac signaling pathways. Interestingly, PAK kinase activity was not required for activation of the Rac pathway, but was shown to be important in the disassembly of the focal complexes. PAK1 has also been reported to induce filopodia and lamellipodia similar to those induced by Cdc42Hs and Rac. However, these cytoskeletal changes occur independently of PAK1's ability to bind Cdc42Hs and Rac, and are partly independent of its kinase activity. These results, coupled with the results from experiments using effector mutants of Rac and Cdc42Hs suggest that, while PAK1 may be able to induce cytoskeletal changes when it is overexpressed, it might not be the link between GTPases and the cytoskeleton.

Recent studies indicated that Cdc42Hs is localized to the BFA sensitive compartment of the Golgi apparatus. The role of Cdc42Hs in the Golgi is poorly understood. The Golgi apparatus is known mostly for its roles in the formation of transport vesicles which carry cargo to a receiving compartment. Nonclathrin coat proteins such as bCOP and the GTPase ARF were shown to be implicated in Golgi mediated transport. Disruption of the coatomer complexes by treating cells with BFA or expressing dominant negative forms of ARF blocked the transport of vesicles to the plasma membrane. These data indicated that PAK4 is co-localized with bCOP and is redistributed by treating the cells with BFA. Furthermore, BFA treatment affected the filopodia formation and actin polymerization induced by PAK4 and Cdc42HsV12. Interestingly, it was previously reported that fibroblast treated with BFA failed to make filopodia and lamellipodia and subsequently cells were defective in motility. It has been proposed that the disruption of the Golgi apparatus by BFA may affect the supply of vesicles containing the components necessary for the formation of filopodia. Because it is localized by Cdc42Hs to the Golgi, PAK4 is a good candidate for an effector molecule that transduces a Cdc42Hs dependent signal from the Golgi. It is conceivable that PAK4 and Cdc42Hs regulate the re-organization of actin and the formation of filopodia by controlling the transport of vesicles containing the proteins and/or lipids necessary for the induction of morphological changes. Interestingly, in addition to the induction of filopodia, PAK4 also leads to localized actin polymerization at the Golgi area. In future studies it will be interesting to determine whether actin polymerization in this area is important for vesicle fusion or other aspects of Golgi function.

In summary, PAK4 provides a molecular link between Cdc42Hs and actin rearrangement, and suggests involvement of the Golgi apparatus in cell morphogenesis. Understanding how PAK4 together with Cdc42Hs and putative targets at the Golgi control the reorganization of the actin cytoskeleton will contribute to the understanding of the molecular mechanism of morphogenesis.

SECOND SERIES OF EXPERIMENTS

Mouse PAK4 Sequences

1) Partial cDNA of the Mouse PAK4:

```
AAGCAGCAGC GGCGCGAGTT GCTCTTCAAT GAGGTGGTGA TCATGCGGGA  (SEQ ID NO: 13)

CTACCGGCAC GAGAACGTGG TGGAGATGTA CAACAGCTAC CTGGTGGGTG

ACGAACTCTG GGTCGTCATG GAGTTCCTGG AAGGCGGCGC CCTCACGGAT

ATTGTCACCC ACACCAGGAT GAACGAGGAA CAGATCGCCG CCGTGTGCCT

GGCTGTGCTT CAGGCGCTGG CTGTGCTCCA CGCCCAGGGT GTCATCCACA

GCGACATAAA AACGGACA
```

2) Predicted Amino Acid Sequence of the Partial Mouse PAK4 cDNA:

```
KQQRRELLFN EVVIMRDYRH ENVVEMYNSY LVGDELWVVM EFLEGGALTD (SEQ ID NO: 14)

IVTHTRMNEE QIAAVCLAVL QALAVLHAQG VIHSDIKTD
```

3) Partial Genomic Sequence of Mouse PAK4:

```
ACCTGGTGGG TGACGAACTC TGGGTCGTCA TGGAGTTCCT GGAAGGCGGC (SEQ ID NO: 15)

GCCCTCACGG ATATTGTCAC CCACACCAGG TACCATAGGG CAGCCTGCTG

GCTCATGTGC TCCCTGGGGT GGAACTGGGA CCCTTTAGGC TCTGGTGATA

GACAAGTGCC CTCCAGAGTG TGGGTGGGGC AGTGAGGCCA GGCACACAGG

ATGGGGGTCA TAGCATCGTG GCTCCCTGAC CCCTGTTGAG GCGGGTCTTT

GTGACCTCTT GTTGTCTAAA GCAGGGTAGG GGCCTCTTCA CTGCCCACTC

TCACCCCAGG GTGGGATGCC CAAGGCAGCG CTGAGTGCCC AGTTGCTCCT

CTGCCCGCGC AGGATGAACG AGGAACAGAT CGCCGCCCGT GTGCCTGGCT

TGTGCTTCAN GCGCTGGCTT GTGCTCCACG CCCAGGGTGT CATCCACCGT

GACATCAAGA GTGACTCTAT CTTGCTGACC CATGATGGC
```

METHODS

1) Isolation of the Partial Mouse CDNA:

The partial mouse cDNA was generated by degenerate PCR using degenerate primers corresponding to the following amino acid sequences: (a) GEGSTG (SEQ ID NO: 16) (b) SLVGTP (SEQ ID NO: 17) within the kinase domain of PAK4. The degenerate primers were used in a PCR reaction using mouse cDNA (from NIH3T3 cells) as a template.

2) Isolation of the Full Length Mouse PAK4;

The paertial cDNA is currently being used to isolate the full length PAK4cDNA. Th epartial cDNA will be used as a probe to screen a mouse brain cDNA library (Stratagene). Nylon transfer filters containing $1 \times 10^6$ recombinant plaques will be hybridized with the randomlyprimed [α-32P] dCTP-labeled probe (Prime-It II kit, Stratagene) overnight at 42° C. in 6×SSC, 50% formamide, 0.1% SDS and washed at 65° C. in 2×SSC, 0.1% SDS according to standard protocol. Positive plaques will be taken through further purification and excised in vivo as plasmids. The positive inserts will be sequenced in both strands. If necessary, 5' RACE and 3' RACE will be carried out to isolate the 5' and 3' ends.

3) Isolation of the Mouse Genomic Sequence:

The partial mouse CDNA was used as a probe to screen a BAC system (Bacterial Artificial Chromosome) mouse genomic library (Genome Systems). Positive clones were subcloned into a Bluescript vector and analyzed by Southern Blots and sequencing. One of the positive clones (8 kb) has been sequenced partially, and found to contain the sequence shown above. This clone will be further sequenced to determine whether it contatins the full length genomic PAK4 sequence, it will be used as a probe to undergo a further round of screening, until the full length sequence is isolated.

REFERENCES

Aspenstrom, P., Lindberg, U., and Hall, A. (1996). Two GTPases, Cdc42 and Rac, bind directly to a protein implicated in the immunodeficiency disorder Wiskott-Aldrich syndrome. Curr Biol 6, 70–75.

Bagrodia, S., Derijard, B., Davis, R. J., and Cerione, R. A. (1995). Cdc42 and PAK-mediated signaling leads to Jun kinase and p38 mitogen-activated protein kinase activation. J Biol Chem 270, 27995–27998.

Bashour, A. M., Fullerton, A. T., Hart, M., and Bloom, G. S. (1997). IQGAP1, a Rac- and Cdc42-binding protein, directly binds and cross-links microfilaments. J Cell Biol 137, 1555–1566.

Benner, G. E., Dennis, P. B., and Masaracchia, R. A. (1995). Activation of an S6/H4 kinase (PAK 65) from human placenta by intramolecular and intermolecular autophosphorylation. J Biol Chem 270, 21121–21128.

Bershadsky, A., and Futerman, A. (1994). Disruption of the Golgi apparatus by brefeldin A blocks cell polarization and inhibits directed cell migration. Proc Natl Acad Sci U.S.A. 91, 5686–5689.

Brown, J. L., Stowers, L., Baer, M., Trejo, J., Coughlin, S., and Chant, J. (1996). Human Ste20 homologue hPAK1 links GTPases to the JNK MAP kinase pathway. Curr Biol 6, 598–605.

Burbelo, P. D., Drechsel, D., and Hall, A. (1995). A conserved binding motif defines numerous candidate target proteins for both Cdc42 and Rac GTPases. J Biol Chem 270, 29071–29074.

Coso, O. A., Chiariello, M., Yu, J. C., Teramoto, H., Crespo, P., Xu, N., Miki, T., and Gutkind, J. S. (1995). The small GTP-binding proteins Rac1 and Cdc42 regulate the activity of the JNK/SAPK signaling pathway. Cell 81, 1137–1146.

Cvrckova, F., De Virgilio, C., Manser, E., Pringle, J. R., and Nasmyth, K. (1995). Ste20-like protein kinases are required for normal localization of cell growth and for cytokinesis in budding yeast. Genes Dev. 9, 1817–1830.

Dascher, C., and Balch, W. E. (1994). Dominant inhibitory mutants of ARF1 block endoplasmic reticulum to Golgi transport and trigger disassembly of the Golgi apparatus. J Biol Chem 269, 1437–48.

Dharmawardhane, S., Sanders, L. C., Martin, S. S., Daniels, H., and Bokoch, G. M. (1997). Localization of p21-activated kinase 1 (PAK1) to pinocytic vesicles and cortical actin structures in stimulated cells. J Cell Biol 138, 1265–1278.

Donaldson, J. G., Cassel, D., Kahn, R. A., and Klausner, R. D. (1992). ADP-ribosylation factor, a small GTP-binding protein, is required for binding of the coatomer protein beta-COP to Golgi membranes. Proc Natl Acad Sci USA 89, 6408–12.

Donaldson, J. G., Finzaai, D., and Klausner, R. D. (1992). Brefaldin A inhibits golgi membrane-catalysed exchange of guanine nucleotide into ARF protein. Nature 360, 350–352.

Dutartre, H., Davoust, J., Gorvel, J. P., and Chavrier, P. (1996). Cytokinesis arrest and redistribution of actin-cytoskeleton regulatory components in cells expressing the Rho GTPase CDC42Hs. J Cell Sci 109, 367–377.

Erickson, J. W., Cerione, R. A., and Hart, M. J. (1997). Identification of an actin cytoskeletal complex that includes IQGAP and the Cdc42 GTPase. J Biol Chem 272, 24443.

Erickson, J. W., Zhang, C. j., Kahn, R. A., Evans, T., and Cerione, R. A. (1996). Mammalian Cdc42 is a brefeldin A-sensitive component of the Golgi apparatus. J Biol Chem 271, 26850–26854.

Fukata, M., Kuroda, S., Fujii, K., Nakamura, T., Shoji, I., Matsuura, Y., Okawa, K., Iwamatsu, A., Kikuchi, A., and Kaibuchi, K. (1997). Regulation of cross-linking of actin filament by IQGAP1, a target for Cdc42. J Biol Chem 272, 29579–29583.

Hanks, S. K., Quinn, A. M., and Hunter, T. (1988). The protein kinase family: conserved features and deduced phylogeny of the catalytic domains. Science 241, 42–52.

Hart, M.J., Callow, M.G., Souza, B., Polakis, P. (1996). IQGAP, a colmodulin-binding protein with a rasGAP-related domain, is a potential effector for cdc4Hs. EMBO J. 15, 2997–3005.

Helms, J. B., and Rothman, J. E. (1992). Inhibition by brefeldin A of a golgi membrane enzyme that catalyses exchange of guanine nucleotide bound to ARF. Nature 360, 352–354.

Johnson, L., N., Noble, M. E., and Owen, D. J. (1996). Active and inactive protein kinases: structural basis for regulation. Cell 85, 149–158.

Joneson, T., McDonough, M., Bar-Sagi, D., and Van Aelst, L. (1996). RAC regulation of actin polymerization and proliferation by a pathway distinct from Jun kinase. Science 274, 1374–1376.

Kozma, R., Ahmed, S., Best, A., and Lim, L. (1995). The Ras-related protein Cdc42Hs and bradykinin promote formation of peripheral actin microspikes and filopodia in Swiss 3T3 fibroblasts. Mol Cell Biol 15, 1942–1952.

Kuroda, S., Fukata, M., Kobayashi, K., Nakafuku, M., Nomura, N., Iwamatsu, A., Kaibuchi, K. (1996). Identification of IQGAP as a putative target for the small GTPases, Cdc42 and Rac1. J. Bio. chem. 271, 23363–23367.

Lamarche, N., Tapon, N., Stowers, L., Burbelo, P. D., Aspenstrom, P., Bridges, T., Chant, J., and Hall, A. (1996). Rac and Cdc42 induce actin polymerization and Gi cell cycle progression independently of p65PAK and the JNK/SAPK MAP kinase cascade. Cell 87, 519–529.

Manser, E., Huang, H. Y., Loo, T. H., Chen, X. Q., Dong, J. M., Leung, T., and Lim, L. (1997). Expression of constitutively active alpha-PAK reveals effects of the kinase on actin and focal complexes. Mol Cell Biol 17, 1129–1143.

Manser, E., Leung, T., Salihuddin, H., Zhao, Z. S., and Lim, L. (1994). A brain serine/threonine protein kinase activated by Cdc42 and Rac1. Nature 367, 40–46.

Manser, E., Leun, T., Salihuddin, H., Tan, L., and Lim, L. (1993). A non-receptor tyrosine kinase that inhibits the GTPase activity of p2lcdc42. Nature 363, 364–367.

Manser, E., Loo, T., Koh, C.-G., Zhao, Z.-S., Chen, X.-Q., Tan, L., Tan, I., Leung, T., and Lim, L. (1998). PAK kinases are directly coupled to the PIX family of nucleotide exchange factors. Mol Cell 1, 183–192.

Marshall, C. J. (1994). Signal transduction. Hot lips and phosphorylation of protein kinases. Nature 367, 686.

Martin, G. A., Bollag, G., McCormick, F., and Abo, A. (1995). A novel serine kinase activated by rac1/CDC42Hs-dependent autophosphorylation is related to PAK65 and STE20. EMBO J 14, 1970–1978.

Minden, A., Lin, A., Claret, F. X., Abo, A., and Karin, M. (1995). Selective activation of the JNK signaling cascade and c-Jun transcriptional activity by the small GTPases Rac and Cdc42Hs. Cell 81, 1147–1157.

Minden, A., Lin, A., McMahon, M., Lange-Carter, C., Derijard, B., Davis, R. J., Johnson, G. L., and Karin, M. (1994). Differential activation of ERK and JNK mitogen-activated protein kinases by Raf-1 and MEKK. Science 266, 1719–1723.

Nobes, C. D., and Hall, A. (1995). Rho, rac, and cdc42 GTPases regulate the assembly of multimolecular focal complexes associated with actin stress fibers, lamellipodia, and filopodia. Cell 81, 53–62.

Orci, L., Tagaya, M., Amherdt, M., Perrelet, A., Donaldson, J. G., Lippincott-Schwartz, J., Klausner, R. D., and Rothman, J. E. (1991). Brefeldin A, a drug that blocks secretion, prevents the assembly of non-clathrin-coated buds on Golgi cisternae. Cell 64, 1183–1195.

Pelech, S. L. (1996). Kinase connections on the cellular intranet. Signalling pathways. Curr Biol 6, 551–554.

Rana, A., Gallo, K., Godowski, P., Hirai, S., Ohno, S., Zon, L., Kyriakis, J. M., and Avruch, J. (1996). The mixed lineage kinase SPRK phosphorylates and activates the stress-activated protein kinase activator, SEK-1. J Biol Chem 271, 19025–19028.

Schekman, R., and Orci, L. (1996). Coat proteins and vesicle budding. Science 271, 1526–1533.

Sells, M. A., and Chernof, J. (1997). Emerging from the Pak: the p21-activated protein kinase family. Trends Cell Biol 7, 162–167.

Sells, M. A., Knaus, U. G., Bagrodia, S., Ambrose, D. M., Bokoch, G. M., and Chernoff, J. (1997). Human p21-activated kinase (Pak1) regulates actin organization in mammalian cells. Curr Biol 7, 202–210.

Symons, M., Derry, J. M., Karlak, B., Jiang, S., Lemahieu, V., McCormick, F., U., F., and Abo, A. (1996). Wiskott-Aldrich syndrome protein, a novel effector for the GTPase CDC42Hs, is implicated in actin polymerization. Cell 84, 723–734.

Szczepanowska, J., Zhang, X., Herring, C., Qin, J., Korn, E. D., and Brzeska, H. (1997). Identification by mass spectrometry of the phosphorylated residue responsible for activation of the catalytic domain of myosin I heavy chain kinase, a member of the PAK/STE20 family. Proc Natl Acad Sci USA 94, 8503–8508.

Takebe, Y., Seiki, M., Fujisawa, J., Hoy, P., Yokota, K., Arai, K., Yoshida, M., and Arai, N. (1988). SR alpha promoter: an efficient and versatile mammalian cDNA expression system composed of the simian virus 40 early promoter and the R-US segment of human T-cell leukemia virus type 1 long terminal repeat. Mol. Cell. Biol. 8, 466–472.

Teramoto, H., Coso, 0. A., Miyata, H., Igishi, T., Miki, T., and Gutkind, J. S. (1996). Signaling from the small GTP-binding proteins Rac1 and Cdc42 to the c-Jun N-terminal kinase/stress-activated protein kinase pathway. A role for mixed lineage kinase 3/protein-tyrosine kinase 1, a novel member of the mixed lineage kinase family. J Biol Chem 271, 27225–227228.

Van Aelst, L., and D'Souza-Schorey, C. (1997). Rho GTPases and signaling networks. Genes Dev 11, 2295–2322.

Van Aelst, L., Joneson, T., and Bar-Sagi, D. (1996). Identification of a novel Raci-interacting protein involved in membrane ruffling. EMBO J 15, 3778–3786.

Westwick, J. K., Lambert, G. T., Clark, G. J., Symons, M., Van Aelst, L., Pestell, R. G., and Der, C. J. (1997). Rac Regulation of Transformation, Gene Expression, and Actin Organization by Multiple, PAK-Independent Pathways. Mol. Cell. Biol 17, 1324–1335.

Zhang, C. J., Rosenwald, A. G., Willingham, M. C., Skuntz, S., Clark, J., and Kahn, R. A. (1994). Expression of a dominant allele of human ARF1 inhibits membrane traffic in vivo. J Cell Biol 124, 289–300.

Zhang, F., Strand, A., Robbins, D., Cobb, M. H., and Goldsmith, E. J. (1994). Atomic structure of the MAP kinase ERK2 at 2.3 A resolution. Nature 367, 704–711.

Zhang, S., Han, J., Sells, M. A., Chernoff, J., Knaus, U. G., Ulevitch, R. J., and Bokoch, G. M. (1995). Rho family GTPases regulate p38 mitogen-activated protein kinase through the downstream mediator Pakl. J Biol Chem 270, 23934–23936.

What is claimed is:

1. An isolated mammalian PAK4 serine/threonine kinase comprising the amino acid sequence set forth in FIGS. 1A–1B (SEQ ID NO:2).

2. An isolated mammalian PAK4 serine/threonine kinase whose amino acid sequence consists of the amino acid sequence set forth in FIGS. 1A–1B (SEQ ID NO:2).

* * * * *